United States Patent
Girard et al.

(10) Patent No.: US 9,770,441 B1
(45) Date of Patent: Sep. 26, 2017

(54) CRYSTALLINE SOLID FORMS OF 6-CARBOXY-2-(3,5-DICHLOROPHENYL)-BENZOXAZOLE

(71) Applicant: Pfizer Inc., New York, NY (US)

(72) Inventors: Kevin Paul Girard, Quaker Hill, CT (US); Andrew J. Jensen, Ledyard, CT (US); Kris Nicole Jones, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/509,343

(22) PCT Filed: Aug. 31, 2015

(86) PCT No.: PCT/IB2015/056597
§ 371 (c)(1),
(2) Date: Mar. 7, 2017

(87) PCT Pub. No.: WO2016/038500
PCT Pub. Date: Mar. 17, 2016

Related U.S. Application Data

(60) Provisional application No. 62/203,953, filed on Aug. 12, 2015, provisional application No. 62/047,614, filed on Sep. 8, 2014.

(51) Int. Cl.
*C07D 263/57* (2006.01)
*A61K 31/423* (2006.01)

(52) U.S. Cl.
CPC .......... *A61K 31/423* (2013.01); *C07D 263/57* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 5,033,252 A | 7/1991 | Carter | |
| 5,052,558 A | 10/1991 | Carter | |
| 5,323,907 A | 6/1994 | Kalvelage | |
| 7,214,695 B2 | 5/2007 | Kelly et al. | |
| 9,249,112 B2 * | 2/2016 | Labaudiniere | ........... C07H 5/06 |

FOREIGN PATENT DOCUMENTS

WO    2013038351 A1    3/2013

OTHER PUBLICATIONS

Supporting Information for Angew. Chem. Int. Ed., 42:2758 (2003).*
Buxbaum, "The Genetics of the Amyloidoses*". Annu. Rev. Med., 2000, 542-569, 51.
Jacobson, "Variant-Sequence Transthyretin (Isoleucine 122) In Late-Onset Cardiac Amyloidosis in Black Americans." The New England Journal of Medicine, 1997, 466-473, 336, 7.
Kelly, "Partial Denaturation of Transthyretin is Sufficient for Amyloid Fibril Formation in Vitro." Biochemistry, 1992, 8654-8660, 31.
Kelly, "Alternative conformations of amyloidogenic proteins govern their behavior." Current Opinion in Structural Biology, Nov. 17, 1996, 6.
Liu, "A glimpse of a possible amyloidogenic intermediate of transthyretin." Nature Structural Biology, 2000, 754-757, 7, 9.
Penchala, "AG10 inhibits amyloidogenesis and cellular toxicity of the familial amyloid cardiomyopathy-associated V122I transthyretin." PNAS, 2013, 9992-9997, 110, 24.
Razavi, "Benzoxazoles as Transthyretin Amyloid Fibril Inhibitors: Synthesis, Evaluation, and Mechanism of Action**." Angew. Chem. Int. Ed., 2003, 2758-2761, 42.
Saraiva, "Transthyretin Mutations in Health and Disease." Human Mutation, 1995, 191-196, 5.
Saraiva, "Biochemical Marker in Familial Amyloidotic Polyneuropathy, Portuguese Type Family Studies on the Transthyretin (Prealbumin)-Methionine-30 Variant." Journal of Clinical Investigation, 1985, 2171-2177, 76.
Westermark, "Fibril in senile systemic amyloidosis is derived from normal transthyretin." Proc. Natl. Acad. Sci, 1990, 2843-2845, 87.

* cited by examiner

*Primary Examiner* — Michael Barker
(74) *Attorney, Agent, or Firm* — Lisa A. Samuels

(57) ABSTRACT

The present invention relates to solid forms of 6-carboxy-2-(3,5-dichlorophenyl)-benzoxazole and to methods for their preparation. The invention is also directed to pharmaceutical compositions containing at least one solid form and to the therapeutic or prophylactic use of such solid forms and compositions.

16 Claims, 21 Drawing Sheets

FIG. 2

| Angle-2 Theta (2θ) | Intensity (%) |
|---|---|
| 7.0 | 5 |
| 9.7 | 6 |
| 11.8 | 4 |
| 12.4 | 15 |
| 13.0 | 6 |
| 14.1 | 3 |
| 15.4 | 2 |
| 16.5 | 46 |
| 19.4 | 21 |
| 20.2 | 9 |
| 21.2 | 2 |
| 23.5 | 100 |
| 24.2 | 41 |
| 24.5 | 18 |
| 25.0 | 3 |
| 25.6 | 6 |
| 26.4 | 9 |
| 26.7 | 76 |
| 27.1 | 4 |
| 27.4 | 4 |
| 27.6 | 5 |
| 28.0 | 5 |
| 28.6 | 45 |
| 29.0 | 4 |
| 29.6 | 2 |

| Angle-2 Theta (2θ) | Intensity (%) |
|---|---|
| 29.9 | 4 |

FIG. 4

| Angle-2 Theta (2θ) | Intensity (%) |
|---|---|
| 7.0 | 6 |
| 9.8 | 10 |
| 11.6 | 14 |
| 12.3 | 7 |
| 13.2 | 10 |
| 14.1 | 10 |
| 15.9 | 7 |
| 16.7 | 23 |
| 16.9 | 45 |
| 18.0 | 5 |
| 19.2 | 15 |
| 19.7 | 5 |
| 20.8 | 9 |
| 21.2 | 4 |
| 23.4 | 6 |
| 24.1 | 37 |
| 24.7 | 19 |
| 25.3 | 6 |
| 26.1 | 9 |
| 26.8 | 7 |
| 27.3 | 100 |
| 27.9 | 10 |
| 29.4 | 4 |
| 29.8 | 4 |

FIG. 6

| Peak (cm-1) | Intensity (W = weak, M = medium, S = strong) | Peak (cm-1) | Intensity (W = weak, M = medium, S = strong) |
|---|---|---|---|
| 173 | W | 1078 | W |
| 213 | W | 1089 | W |
| 225 | W | 1125 | W |
| 263 | W | 1144 | W |
| 278 | W | 1197 | W |
| 287 | W | 1235 | W |
| 396 | W | 1245 | W |
| 412 | W | 1273 | M |
| 416 | W | 1292 | W |
| 431 | W | 1310 | W |
| 601 | W | 1350 | W |
| 668 | W | 1411 | W |
| 726 | W | 1428 | W |
| 756 | W | 1441 | W |
| 780 | W | 1487 | W |
| 851 | W | 1548 | S |
| 861 | W | 1572 | W |
| 869 | W | 1590 | M |
| 884 | W | 1615 | S |
| 937 | W | 3066 | W |
| 947 | W | 3076 | W |
| 983 | W | | |
| 994 | M | | |
| 1062 | W | | |

FIG. 8

| Peak (cm-1) | Intensity (W = weak, M = medium, S = strong) | Peak (cm-1) | Intensity (W = weak, M = medium, S = strong) |
|---|---|---|---|
| 173 | W | 1088 | W |
| 201 | W | 1124 | W |
| 217 | W | 1145 | W |
| 226 | W | 1195 | W |
| 266 | W | 1234 | W |
| 283 | W | 1247 | W |
| 397 | W | 1273 | M |
| 411 | W | 1297 | W |
| 416 | W | 1309 | W |
| 431 | W | 1351 | W |
| 602 | W | 1411 | W |
| 668 | W | 1430 | W |
| 727 | W | 1439 | W |
| 755 | W | 1486 | W |
| 778 | W | 1547 | S |
| 851 | W | 1573 | W |
| 859 | W | 1590 | M |
| 886 | W | 1613 | S |
| 937 | W | 3066 | W |
| 945 | W | 3074 | W |
| 983 | W | | |
| 994 | M | | |
| 1060 | W | | |
| 1077 | W | | |

FIG. 10

| $^{13}$C Chemical Shifts (ppm) |
|---|
| 111.1 |
| 120.8 |
| 124.1 |
| 125.2 |
| 127.7 |
| 128.6 |
| 131.0 |
| 135.8 |
| 136.6 |
| 139.0 |
| 139.6 |
| 144.7 |
| 149.4 |
| 161.4 |
| 172.2 |

FIG. 12

| ¹³C Chemical Shifts (ppm) |
|---|
| 171.9 |
| 161.3 |
| 149.4 |
| 144.4 |
| 140.1 |
| 139.1 |
| 136.8 |
| 135.7 |
| 130.7 |
| 128.5 |
| 125.4 |
| 124.4 |
| 122.1 |
| 110.7 |

FIG. 15

| Angle-2 Theta (2θ) | Intensity (%) |
|---|---|
| 6.0 | 19 |
| 6.4 | 21 |
| 13.6 | 21 |
| 16.3 | 13 |
| 19.3 | 16 |
| 20.4 | 27 |
| 21.4 | 8 |
| 22.7 | 12 |
| 23.5 | 43 |
| 23.8 | 31 |
| 24.2 | 21 |
| 24.8 | 15 |
| 26.9 | 18 |
| 27.5 | 100 |

FIG. 17

| Peak (cm-1) | Intensity (W = weak, M = medium, S = strong) | Peak (cm-1) | Intensity (W = weak, M = medium, S = strong) |
|---|---|---|---|
| 172 | W | 995 | M |
| 199 | W | 1060 | W |
| 218 | W | 1077 | W |
| 223 | W | 1088 | W |
| 266 | W | 1125 | W |
| 276 | W | 1147 | W |
| 287 | W | 1195 | W |
| 396 | W | 1234 | W |
| 411 | W | 1246 | W |
| 430 | W | 1274 | M |
| 602 | W | 1299 | W |
| 671 | W | 1307 | W |
| 677 | W | 1351 | W |
| 726 | W | 1415 | W |
| 756 | W | 1434 | W |
| 778 | W | 1439 | W |
| 851 | W | 1484 | W |
| 867 | W | 1547 | S |
| 938 | W | 1573 | W |
| 947 | W | 1591 | M |
| 984 | W | 1613 | S |

FIG. 19

| $^{13}$C Chemical Shifts (ppm) |
| --- |
| 109.7 |
| 110.9 |
| 121.2 |
| 125.0 |
| 126.4 |
| 127.0 |
| 128.8 |
| 131.5 |
| 137.2 |
| 144.8 |
| 149.3 |
| 161.3 |
| 172.1 |

CRYSTALLINE SOLID FORMS OF 6-CARBOXY-2-(3,5-DICHLOROPHENYL)-BENZOXAZOLE

CROSS REFERENCE TO RELATED APPLICATIONS

This Application is the national stage filing under 35 U.S.C. 371 of Patent Cooperation Treaty Patent Application No. PCT/IB2015/056597, filed Aug. 31, 2015, which claims the benefit of U.S. Provisional Application No. 62/203,953 filed on Aug. 12, 2015, and U.S. Provisional Application No. 62/047,614 filed on Sep. 8, 2014, which are hereby incorporated by reference in their entirety.

BACKGROUND OF THE INVENTION

This invention relates crystalline forms of 6-carboxy-2-(3,5-dichlorophenyl)-benzoxazole and methods of preparing and using the same.

Synthetic routes for 6-carboxy-2-(3,5-dichlorophenyl)-benzoxazole (hereinafter "the compound of Formula I") are described in U.S. Pat. No. 7,214,695 and solid forms of the meglumine salt of the compound of Formula I are described in U.S. patent application Ser. No. 14/345,111, which is the U.S. national phase of International Application No. PCT/IB2012/054748, all of which are hereby incorporated herein by reference in their entireties for all purposes, and has the structure shown below.

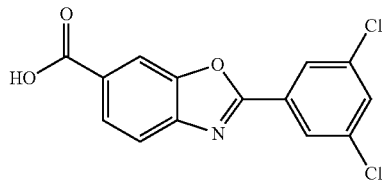

The compound of Formula I stabilizes the protein transthyretin (TTR), dissociation of which is implicated in TTR amyloidosis (i.e., the compound of Formula I prevents dissociation of the native TTR tetramer into monomers, which results in the inhibition of TTR amyloid fibril formation) and is being developed for use in the treatment of transthyretin amyloid diseases.

Solid forms are of interest to the pharmaceutical industry and especially to those involved in the development of suitable dosage forms. If the solid form is not held constant during clinical or stability studies, the exact dosage form used or studied may not be comparable from one lot to another. It is also desirable to have processes for producing a compound with the selected solid form in high purity when the compound is used in clinical studies or commercial products since impurities present may produce undesired toxicological effects. Certain solid forms may also exhibit enhanced stability or may be more readily manufactured in high purity in large quantities, and thus are more suitable for inclusion in pharmaceutical formulations. Certain solid forms may display other advantageous physical properties such as lack of hygroscopic tendencies, filterability, improved solubility, and enhanced rates of dissolution due to different lattice energies.

The discussion of the background to the invention herein is included to explain the context of the present invention. This is not to be taken as an admission that any of the material referred to was published, known, or part of the common general knowledge in any country as of the priority date of any of the claims.

SUMMARY OF THE INVENTION

Solid forms of the compound of Formula I are disclosed herein, wherein each solid form can be uniquely identified by several different analytical parameters, alone or in combination, such as, but not limited to: powder X-ray diffraction pattern peaks or combinations of two or more peaks; solid state NMR 13C chemical shifts or combinations of two or more chemical shifts; and Raman shift peaks or combinations of two or more Raman shift peaks.

Based on the disclosure provided herein, one of ordinary skill in the art would appreciate that a first crystalline form of the compound of Formula I (referred to herein as "Form 1") can be uniquely identified by several different spectral peaks or patterns in varying combinations. Described below are exemplary combinations of characteristic peak values that can be used to identify Form 1 and in no way should these exemplary combinations be viewed as limiting other peak value combinations disclosed herein.

One aspect of the present invention provides Form 1, wherein said form has a powder X-ray diffraction pattern comprising peaks at diffraction angles (2θ) of 15.4±0.2 and 20.2±0.2. In another embodiment, Form 1 has a powder X-ray diffraction pattern comprising peaks at diffraction angles (2θ) of 15.4±0.2, 20.2±0.2, and 28.6±0.2. In another embodiment, Form 1 has a powder X-ray diffraction pattern comprising peaks at diffraction angles (2θ) of 15.4±0.2, 20.2±0.2, 28.6±0.2 and 29.0±0.2. In another embodiment, Form 1 has a powder X-ray diffraction pattern comprising peaks at diffraction angles (2θ) of 15.4±0.2, 20.2±0.2, 23.5±0.2, 28.6±0.2 and 29.0±0.2.

One aspect of the present invention provides Form 1, wherein said form has a powder X-ray diffraction pattern comprising peaks at diffraction angles (2θ) of 16.5±0.2, 26.7±0.2, and 28.6±0.2. In another embodiment, Form 1 has a powder X-ray diffraction pattern comprising peaks at diffraction angles (2θ) of 16.5±0.2, 26.7±0.2, 28.6±0.2 and 29.0±0.2. In another embodiment, Form 1 has a powder X-ray diffraction pattern comprising peaks at diffraction angles (2θ) of 15.4±0.2, 16.5±0.2, 26.7±0.2, 28.6±0.2 and 29.0±0.2.

Another aspect of the present invention provides Form 1, wherein said form has a powder X-ray diffraction pattern comprising peaks at diffraction angles (2θ) essentially the same as shown in FIG. 1.

Another aspect of the present invention provides Form 1, wherein said form has a powder X-ray diffraction pattern comprising peaks at diffraction angles (2θ) essentially the same as shown in FIG. 21.

Another aspect of the present invention provides Form 1, wherein said form has a Raman spectrum comprising Raman shift peaks (cm-1) at 287±2, 869±2, and 1292±2. In another embodiment, Form 1 has a Raman spectrum comprising Raman shift peaks (cm-1) at 213±2, 287±2, 869±2, and 1292±2.

Another aspect of the present invention provides Form 1, wherein said form has a Raman spectrum comprising Raman shift peaks (cm-1) at 994±2, 1273±2, 1292±2 and 1615±2. In another embodiment, Form 1 has a Raman spectrum comprising Raman shift peaks (cm-1) at 213±2, 994±2, 1273±2, 1292±2 and 1615±2.

Another aspect of the present invention provides Form 1, wherein said form has a Raman spectrum comprising Raman shift peaks (cm-1) at positions essentially the same as shown in FIG. 5.

Another aspect of the present invention provides Form 1, wherein said form has a solid state NMR spectrum comprising 13C chemical shifts (ppm) at 120.8±0.2, 127.7±0.2, and 139.6±0.2. In another embodiment, Form 1 has a solid state NMR spectrum comprising 13C chemical shifts (ppm) at 127.7±0.2 and 139.6±0.2. In another embodiment, Form 1 has a solid state NMR spectrum comprising 13C chemical shifts (ppm) at 120.8±0.2 and 139.6±0.2. In another embodiment, Form 1 has a solid state NMR spectrum comprising 13C chemical shifts (ppm) at 120.8±0.2 and 127.7±0.2.

Another aspect of the present invention provides Form 1, wherein said form has a solid state NMR spectrum comprising 13C chemical shifts (ppm) at 120.8±0.2, 127.7±0.2, and 144.7±0.2. In another embodiment, Form 1 has a solid state NMR spectrum comprising 13C chemical shifts (ppm) at 127.7±0.2 and 144.7±0.2. In another embodiment, Form 1 has a solid state NMR spectrum comprising 13C chemical shifts (ppm) at 120.8±0.2 and 144.7±0.2. In another embodiment, Form 1 has a solid state NMR spectrum comprising 13C chemical shifts (ppm) at 120.8±0.2 and 127.7±0.2.

Another aspect of the present invention provides Form 1, wherein said form has a solid state NMR spectrum comprising 13C chemical shifts (ppm) at positions essentially the same as shown in FIG. 9.

Another aspect of the present invention provides Form 1, wherein said form (i) has a powder X-ray diffraction pattern comprising peaks at diffraction angles (2θ) of 15.4±0.2, 20.2±0.2, and 28.6±0.2; and (ii) has a Raman spectrum comprising Raman shift peaks (cm-1) at 287±2, 869±2, and 1292±2.

Another aspect of the present invention provides Form 1, wherein said form (i) has a powder X-ray diffraction pattern comprising a peak at a diffraction angle (2θ) of 28.6±0.2; and (ii) has a Raman spectrum comprising Raman shift peaks (cm-1) at 287±2, 869±2, and 1292±2.

Another aspect of the present invention provides Form 1, wherein said form (i) has a powder X-ray diffraction pattern comprising peaks at diffraction angles (2θ) of 15.4±0.2, 20.2±0.2, and 28.6±0.2; and (ii) has a solid state NMR spectrum comprising 13C chemical shifts (ppm) at 120.8±0.2 and 139.6±0.2.

Another aspect of the present invention provides Form 1, wherein said form (i) has a powder X-ray diffraction pattern comprising peak at a diffraction angles (2θ) of 28.6±0.2; and (ii) has a solid state NMR spectrum comprising 13C chemical shifts (ppm) at 120.8±0.2 and 139.6±0.2.

Another aspect of the present invention provides Form 1, wherein said form (i) has a powder X-ray diffraction pattern comprising peaks at diffraction angles (2θ) of 26.7±0.2 and 28.6±0.2; and (ii) has a solid state NMR spectrum comprising 13C chemical shifts (ppm) at 127.7±0.2.

Another aspect of the present invention provides Form 1, wherein said form (i) has a Raman spectrum comprising Raman shift peaks (cm-1) at 287±2, 869±2, and 1292±2; and (ii) has a solid state NMR spectrum comprising 13C chemical shifts (ppm) at 120.8±0.2 and 139.6±0.2.

Another aspect of the present invention provides Form 1, wherein said form (i) has a Raman spectrum comprising Raman shift peaks (cm-1) at 994±2, 1273±2, and 1292±2; and (ii) has a solid state NMR spectrum comprising 13C chemical shifts (ppm) at 120.8±0.2 and 127.7±0.2.

Another aspect of the present invention provides Form 1, wherein said form (i) has a Raman spectrum comprising Raman shift peaks (cm-1) at 1292±2 and 1615±2; and (ii) has a solid state NMR spectrum comprising 13C chemical shifts (ppm) at 127.7±0.2.

In certain embodiments, the present invention relates to Form 1, wherein said form is non-hygroscopic and anhydrous.

In certain embodiments, the present invention relates to Form 1, wherein said form comprises a plurality of needles of the compound of Formula I.

In a further aspect, the present invention contemplates that Form 1 can exist in the presence of the any other of the solid forms (e.g. Forms 2, 4 and 6) or mixtures thereof. Accordingly, in one embodiment, the present invention provides Form 1, wherein Form 1 is present in a solid form that includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of the compound of Formula I. For example, in one embodiment is a solid form of the compound of Formula I comprising Form 1 that has any one of the powder X-ray diffraction patterns, Raman spectra, IR spectra and/or NMR spectra described above, wherein said solid form includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of the compound of Formula I.

In certain embodiments, the present invention relates to Form 1, wherein said form is substantially pure crystalline form.

Further, based on the disclosure provided herein, one of ordinary skill in the art would appreciate that a second crystalline form of the compound of Formula I (referred to herein as "Form 4") can be uniquely identified by several different spectral peaks or patterns in varying combinations. Described below are exemplary combinations of characteristic peak values that can be used to identify Form 4 and in no way should these exemplary combinations be viewed as limiting other peak value combinations disclosed herein.

One aspect of the present invention provides Form 4, wherein said form has a powder X-ray diffraction pattern comprising peaks at diffraction angles (2θ) of 15.9±0.2 and 16.9±0.2. In another embodiment, Form 4 has a powder X-ray diffraction pattern comprising peaks at diffraction angles (2θ) of 15.9±0.2, 16.9±0.2 and 18.0±0.2. In another embodiment, Form 4 has a powder X-ray diffraction pattern comprising peaks at diffraction angles (2θ) of 16.9±0.2, 24.1±0.2 and 27.3±0.2. In another embodiment, Form 4 has a powder X-ray diffraction pattern comprising peaks at diffraction angles (2θ) of 15.9±0.2, 16.9±0.2, 18.0±0.2, and 27.3±0.2.

Another aspect of the present invention provides Form 4, wherein said crystalline form has a powder X-ray diffraction pattern comprising peaks at diffraction angles (2θ) essentially the same as shown in FIG. 3.

Another aspect of the present invention provides Form 4, wherein said form has a Raman spectrum comprising Raman shift peaks (cm-1) at 266±2, 283±2, and 1297±2. In another embodiment, Form 4 has a Raman spectrum comprising Raman shift peaks (cm-1) at 201±2, 266±2, 283±2, and 1297±2. In another embodiment, Form 4 has a Raman spectrum comprising Raman shift peaks (cm-1) at 283±2, 994±2, 1273±2, and 1547±2.

Another aspect of the present invention provides Form 4, wherein said form has a Raman spectrum comprising Raman shift peaks (cm-1) at positions essentially the same as shown in FIG. 7.

Another aspect of the present invention provides Form 4, wherein said form has a solid state NMR spectrum comprising 13C chemical shifts (ppm) at 122.1±0.2, 130.7±0.2, and 140.1±0.2. In another embodiment, Form 4 has a solid state NMR spectrum comprising 13C chemical shifts (ppm) at 122.1±0.2, 124.4±0.2, and 130.7±0.2. In another embodiment, Form 4 has a solid state NMR spectrum comprising 13C chemical shifts (ppm) at 130.7±0.2 and 140.1±0.2. In another embodiment, Form 4 has a solid state NMR spectrum comprising 13C chemical shifts (ppm) at 122.1±0.2 and 140.1±0.2. In another embodiment, Form 4 has a solid state NMR spectrum comprising 13C chemical shifts (ppm) at 122.1±0.2 and 130.7±0.2. In another embodiment, Form 4 has a solid state NMR spectrum comprising 13C chemical shifts (ppm) at 124.4±0.2 and 130.7±0.2.

Another aspect of the present invention provides Form 4, wherein said form has a solid state NMR spectrum comprising 13C chemical shifts (ppm) at positions essentially the same as shown in FIG. 11.

Another aspect of the present invention provides Form 4, wherein said form (i) has a powder X-ray diffraction pattern comprising peaks at diffraction angles (2θ) of 15.9±0.2 and 16.9±0.2; and (ii) has a Raman spectrum comprising Raman shift peaks (cm-1) at 266±2, 283±2, and 1297±2. Another aspect of the present invention provides Form 4, wherein said form (i) has a powder X-ray diffraction pattern comprising peaks at diffraction angles (2θ) of 15.9±0.2 and 16.9±0.2; and (ii) has a solid state NMR spectrum comprising 13C chemical shifts (ppm) at 122.1±0.2, 130.7±0.2, and 140.1±0.2.

Another aspect of the present invention provides Form 4, wherein said form (i) has a Raman spectrum comprising Raman shift peaks (cm-1) at 266±2, 283±2, and 1297±2; and (ii) has a solid state NMR spectrum comprising 13C chemical shifts (ppm) at 122.1±0.2, 130.7±0.2, and 140.1±0.2.

In certain embodiments, the present invention relates to Form 4, wherein said form is non-hygroscopic and anhydrous.

In certain embodiments, the present invention relates to Form 4, wherein said form comprises a plurality of needles of the compound of Formula I.

In a further aspect, the present invention contemplates that Form 4 can exist in the presence of the any other of the solid forms (e.g. Form 1, 2 and 6) or mixtures thereof. Accordingly, in one embodiment, the present invention provides Form 4, wherein Form 4 is present in a solid form that includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of the compound of Formula I. For example, in one embodiment is a solid form of the compound of Formula I comprising Form 4 that has any one of the powder X-ray diffraction patterns, Raman spectra, IR spectra and/or NMR spectra described above, wherein said solid form includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of the compound of Formula I.

In certain embodiments, the present invention relates to Form 4, wherein said form is substantially pure crystalline form.

Further, based on the disclosure provided herein, one of ordinary skill in the art would appreciate that a third crystalline form of the compound of Formula I (referred to herein as "Form 6") can be uniquely identified by several different spectral peaks or patterns in varying combinations. Described below are exemplary combinations of characteristic peak values that can be used to identify Form 6 and in no way should these exemplary combinations be viewed as limiting other peak value combinations disclosed herein.

One aspect of the present invention provides Form 6, wherein said form has a powder X-ray diffraction pattern comprising peaks at diffraction angles (2θ) of 23.8±0.2 and 27.5±0.2. In another embodiment, Form 6 has a powder X-ray diffraction pattern comprising peaks at diffraction angles (2θ) of 13.6±0.2, 23.8±0.2 and 27.5±0.2. In another embodiment, Form 6 has a powder X-ray diffraction pattern comprising peaks at diffraction angles (2θ) of 13.6±0.2, 23.5±0.2, 23.8±0.2, and 27.5±0.2.

Another aspect of the present invention provides Form 6, wherein said crystalline form has a powder X-ray diffraction pattern comprising peaks at diffraction angles (2θ) essentially the same as shown in FIG. 14.

Another aspect of the present invention provides Form 6, wherein said form has a Raman spectrum comprising Raman shift peaks (cm-1) at 223±2, 1274±2, and 1434±2. In another embodiment, Form 6 has a Raman spectrum comprising Raman shift peaks (cm-1) at 223±2, 1274±2, 1434±2, and 1547±2.

Another aspect of the present invention provides Form 6, wherein said form has a Raman spectrum comprising Raman shift peaks (cm-1) at positions essentially the same as shown in FIG. 16.

Another aspect of the present invention provides Form 6, wherein said form has a solid state NMR spectrum comprising 13C chemical shifts (ppm) at 109.7±0.2, 126.4±0.2, and 131.5±0.2. In another embodiment, Form 6 has a solid state NMR spectrum comprising 13C chemical shifts (ppm) at 109.7±0.2 and 126.4±0.2. In another embodiment, Form 6 has a solid state NMR spectrum comprising 13C chemical shifts (ppm) at 126.4±0.2 and 131.5±0.2. In another embodiment, Form 6 has a solid state NMR spectrum comprising 13C chemical shifts (ppm) at 109.7±0.2 and 131.5±0.2.

Another aspect of the present invention provides Form 6, wherein said form has a solid state NMR spectrum comprising 13C chemical shifts (ppm) at positions essentially the same as shown in FIG. 18.

Another aspect of the present invention provides Form 6, wherein said form (i) has a powder X-ray diffraction pattern comprising peaks at diffraction angles (2θ) of 23.8±0.2 and 27.5±0.2; and (ii) has a Raman spectrum comprising Raman shift peaks (cm-1) at 223±2, 1274±2, and 1547±2.

Another aspect of the present invention provides Form 6, wherein said form (i) has a powder X-ray diffraction pattern comprising peaks at diffraction angles (2θ) of 23.8±0.2 and 27.5±0.2; and (ii) has a solid state NMR spectrum comprising 13C chemical shifts (ppm) at 109.7±0.2, 126.4±0.2, and 131.5±0.2.

Another aspect of the present invention provides Form 6, wherein said form (i) has a Raman spectrum comprising Raman shift peaks (cm-1) at 223±2, 1274±2, and 1547±2; and (ii) has a solid state NMR spectrum comprising 13C chemical shifts (ppm) at 109.7±0.2, 126.4±0.2, and 131.5±0.2.

In certain embodiments, the present invention relates to Form 6, wherein said form is non-hygroscopic and anhydrous.

In a further aspect, the present invention contemplates that Form 6 can exist in the presence of the any other of the solid forms (e.g. Form 1, 2 and 4) or mixtures thereof. Accordingly, in one embodiment, the present invention provides Form 6, wherein Form 6 is present in a solid form that includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of the compound of Formula I. For example, in one embodiment is a solid form of the compound of Formula I comprising Form 6 that has any one of the powder X-ray diffraction patterns, Raman spectra, IR spectra and/or NMR spectra described above, wherein said solid form includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of the compound of Formula I.

In certain embodiments, the present invention relates to Form 6, wherein said form is substantially pure crystalline form.

A further aspect of the present invention provides a pharmaceutical composition comprising Form 1, Form 2, Form 4 or Form 6 as described herein. In a further aspect, the invention provides an oral dosage form comprising Form 1, Form 2, Form 4 or Form 6, or any one of the pharmaceutical compositions described herein. For example, in one embodiment the oral dosage form is a tablet, pill or capsule. For example, in one embodiment, the oral dosage form is a tablet or capsule.

In one embodiment the invention provides a tablet comprising Form 1, Form 2, Form 4 or Form 6, or any one of the pharmaceutical compositions described herein. For example, in one embodiment the tablet comprises from about 1 to about 100 mg of Form 1, 2, 4 or 6. Further, for example, the tablet comprises about 10 mg of Form 1, 2, 4 or 6. Even further, for example, the tablet comprises about 20 mg of Form 1, 2, 4 or 6. Even further, for example, the tablet comprises about 30 mg of Form 1, 2, 4 or 6. Even further, for example, the tablet comprises about 40 mg of Form 1, 2, 4 or 6. Even further, for example, the tablet comprises about 50 mg of Form 1, 2, 4 or 6. Even further, for example, the tablet comprises about 60 mg of Form 1, 2, 4 or 6. Even further, for example, the tablet comprises about 70 mg of Form 1, 2, 4 or 6. Even further, for example, the tablet comprises about 80 mg of Form 1, 2, 4 or 6. Even further, for example, the tablet comprises about 90 mg of Form 1, 2, 4 or 6. Even further, for example, the tablet comprises about 100 mg of Form 1, 2, 4 or 6.

In one embodiment the invention provides a soft gelatin capsule comprising Form 1, Form 2, Form 4, Form 6, or any one of the pharmaceutical compositions described herein. For example, in one embodiment the soft gelatin capsule comprises from about 1 to about 100 mg of Form 1, 2, 4 or 6. Further, for example, the soft gelatin capsule comprises about 10 mg of Form 1, 2, 4 or 6. Even further, for example, the soft gelatin capsule comprises about 20 mg of Form 1, 2, 4 or 6. Even further, for example, the soft gelatin capsule comprises about 30 mg of Form 1, 2, 4 or 6. Even further, for example, the soft gelatin capsule comprises about 40 mg of Form 1, 2, 4 or 6. Even further, for example, the soft gelatin capsule comprises about 50 mg of Form 1, 2, 4 or 6. Even further, for example, the soft gelatin capsule comprises about 60 mg of Form 1, 2, 4 or 6. Even further, for example, the soft gelatin capsule comprises about 70 mg of Form 1, 2, 4 or 6. Even further, for example, the soft gelatin capsule comprises about 80 mg of Form 1, 2, 4 or 6. Even further, for example, the soft gelatin capsule comprises about 90 mg of Form 1, 2, 4 or 6. Even further, for example, the soft gelatin capsule comprises about 100 mg of Form 1, 2, 4 or 6.

A further aspect of the present invention provides a method for preparing Form 1 as described in Example 1. A further aspect of the present invention provides a method for preparing Form 4, said method comprising heating Form 1 as described in Example 2. A further aspect of the present invention provides a method for preparing Form 2, said method comprising dissolving Form 1 in THF and evaporating the resulting solution as described in Example 3. A further aspect of the present invention provides a method for preparing Form 6, said method comprising heating Form 1 as described in Example 4.

A further aspect of the present invention provides a method of treating transthyretin amyloid diseases, such as senile systemic amyloidosis (SSA), familial amyloid polyneuropathy (FAP) and familial amyloid cardiomyopathy (FAC), in a mammal, the method comprising administering to the mammal a therapeutically effective amount of Form 1, Form 2, Form 4, Form 6, or any of the pharmaceutical compositions described herein.

BRIEF DESCRIPTION OF THE DRAWINGS

FIG. 2 depicts a corresponding peak list for the PXRD pattern shown in FIG. 1.

FIG. 4 depicts a corresponding peak list for the PXRD pattern shown in FIG. 3.

FIG. 6 depicts a corresponding peak list for the Raman spectrum shown in FIG. 5.

FIG. 8 depicts a corresponding peak list for the Raman spectrum shown in FIG. 7.

FIG. 10 depicts a corresponding peak list for the 13C solid state NMR spectrum shown in FIG. 9. The chemical shifts are referenced to an external sample of solid phase adamantane, setting its upfield resonance to 29.5 ppm.

FIG. 12 depicts a corresponding peak list for the 13C solid state NMR spectrum shown in FIG. 11. The chemical shifts are referenced to an external sample of solid phase adamantane, setting its upfield resonance to 29.5 ppm.

FIG. 15 depicts a corresponding peak list for the PXRD pattern shown in FIG. 14.

FIG. 17 depicts a corresponding peak list for the Raman spectrum shown in FIG. 16.

FIG. 19 depicts a corresponding peak list for the 13C solid state NMR spectrum shown in FIG. 18. The chemical shifts are referenced to an external sample of solid phase adamantane setting its upfield resonance to 29.5 ppm.

DETAILED DESCRIPTION OF THE INVENTION

Figure 1:
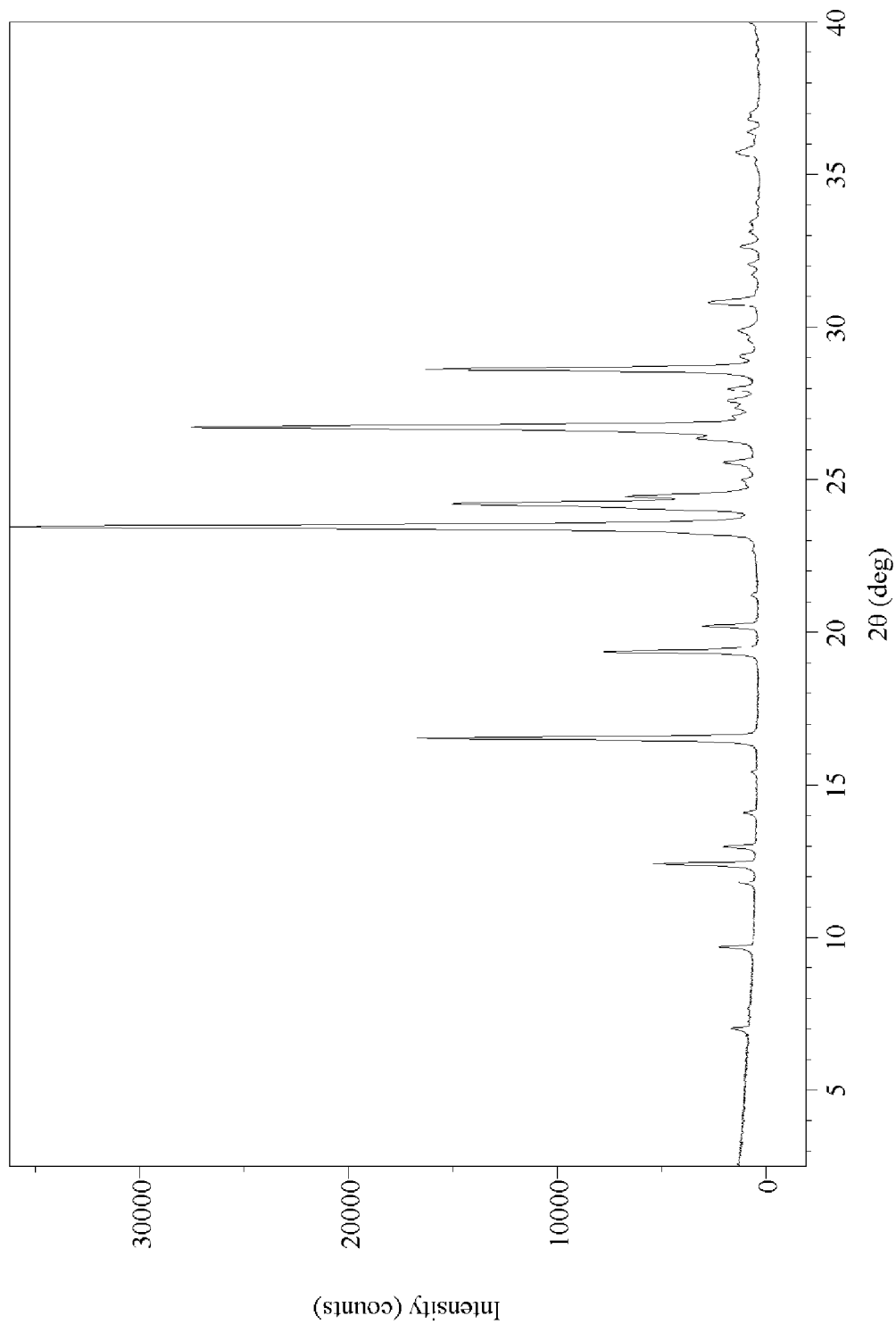
FIG. 1 depicts a characteristic PXRD pattern of Form 1 carried out on a PANalytical X'Pert PRO MPD diffractometer.

Based on a chemical structure, one cannot predict with any degree of certainty whether a compound will crystallize, under what conditions it will crystallize, how many crystalline solid forms of the compound might exist, or the solid-state structure of any of those forms. A key characteristic of any crystalline drug is the polymorphic behavior of such a material. In general, crystalline forms of drugs are preferred over noncrystalline forms of drugs, in part, because of their superior stability. For example, in many situations, a noncrystalline drug converts to a crystalline drug form upon storage. Because noncrystalline and crystalline forms of a drug typically have differing physical properties and chemical properties, such interconversion may be undesirable for safety reasons in pharmaceutical usage. The different physical properties exhibited by different solid forms of a pharmaceutical compound can affect important pharmaceutical parameters such as storage, stability, compressibility, density (important in formulation and product manufacturing), and dissolution rates (important in determining bioavailability). Stability differences may result from changes in chemical reactivity (e.g., differential hydrolysis or oxidation, such that a dosage form comprising a certain polymorph can discolor more rapidly than a dosage form comprising a different polymorph), mechanical changes (e.g., tablets can crumble on storage as a kinetically favored crystalline form converts to thermodynamically more stable crystalline form), or both (e.g., tablets of one polymorph can be more susceptible to breakdown at high humidity). Solubility differences between polymorphs may, in extreme situations, result in transitions to crystalline forms that lack potency and/or that are toxic. In addition, the physical properties of a crystalline form may also be important in pharmaceutical processing. For example, a particular crystalline form may form solvates more readily or may be more difficult to filter and wash free of impurities than other crystalline forms (i.e., particle shape and size distribution might be different between one crystalline form relative to other forms).

There is no one ideal physical form of a drug because different physical forms provide different advantages. The search for the most stable form and for such other forms is arduous and the outcome is unpredictable. Thus it is important to seek a variety of unique drug forms, e.g. salts, polymorphs, non-crystalline forms, which may be used in various formulations. The selection of a drug form for a specific formulation or therapeutic application requires consideration of a variety of properties, and the best form for a particular application may be one which has one specific important good property while other properties may be acceptable or marginally acceptable.

The successful development of a drug requires that it meet certain general requirements to be a therapeutically effective treatment for patients. These requirements fall into two categories: (1) requirements for successful manufacture of dosage forms, and (2) requirements for successful drug delivery and disposition after the drug formulation has been administered to the patient.

Different crystalline solid forms of the same compound often possess different solid-state properties such as melting point, solubility, dissolution rate, hygroscopicity, powder flow, mechanical properties, chemical stability and physical stability. These solid-state properties may offer advantages in filtration, drying, and dosage form manufacturing unit operations. Thus, once different crystalline solid forms of the same compound have been identified, the optimum crystalline solid form under any given set of processing and manufacturing conditions may be determined as well as the different solid-state properties of each crystalline solid form.

Polymorphs of a molecule can be obtained by a number of methods known in the art. Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (PXRD), single crystal X-ray diffractometry, solid state nuclear magnetic resonance (NMR), infrared (IR) spectroscopy, Raman spectroscopy, and hot-stage optical microscopy. For drug development, it is important to provide a compound form (commonly known as a drug substance) that not only is reliably prepared and purified on a large scale, but is also stable and does not degrade on storage. Furthermore, the drug substance must be suitable for formulation in a dosage form chosen according to the intended route of administration.

It has been found that the compound of Formula I can exist in unique crystalline forms, referred to as Form 1, Form 2, Form 4 and Form 6 herein. These forms may be used in a formulated product for the treatment of transthyretin amyloid diseases. As noted above, each form may have advantages over the others in terms of properties such as bioavailability, stability, and manufacturability. In one aspect of the invention, crystalline forms of the compound of Formula I, namely Form 1, Form 2, Form 4 and Form 6, have been discovered which are likely to be more suitable for bulk preparation and handling than the amorphous form. Processes for producing Form 1, Form 2, Form 4 and Form 6 in high purity are described herein. Another object of the present invention is to provide a process for the preparation of each solid form of the compound of Formula I, substantially free from other solid forms. Additionally it is an object of the present invention to provide pharmaceutical formulations comprising the compound of Formula I in different solid forms as discussed above, and methods of treating transthyretin amyloid diseases by administering such pharmaceutical formulations.

Definitions

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of "treating" as defined immediately above.

As used herein, transthyretin or TTR is a 55 kDa homotetramer characterized by 2,2,2 symmetry, having two identical funnel-shaped binding sites at the dimer-dimer interface, where thyroid hormone (T4) can bind in blood plasma and CSF. TTR is typically bound to less than 1 equivalents of holo retinol binding protein. TTR is a 127-residue protein that tetramerizes under physiological conditions. TTR serves as the tertiary transporter of thyroxine in the serum and the primary carrier in the cerebrospinal fluid. TTR also transports retinol through its association with retinol binding protein. TTR forms amyloid at low pH.

As used herein, the term "substantially pure" with reference to a particular crystalline form means that the crystalline or amorphous form includes less than 10%, preferably less than 5%, preferably less than 3%, preferably less than 1% by weight of any other physical forms of the compound.

As used herein, the term "essentially the same" with reference to X-ray diffraction peak positions means that typical peak position and intensity variability are taken into account. For example, one skilled in the art will appreciate that the peak positions (2θ) will show some variability, typically as much as 0.1 to 0.2 degrees, as well as on the apparatus being used to measure the diffraction. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. Similarly, as used herein, "essentially the same" with reference to solid state NMR spectra and Raman spectra is intended to also encompass the variabilities associated with these analytical techniques, which are known to those of skill in the art. For example, 13C chemical shifts measured in solid state NMR will typically have a variability of up to 0.2 ppm for well-defined peaks, and even larger for broad lines, while Raman shifts will typically have a variability of about 2 cm-1.

The term "polymorph" refers to different crystalline forms of the same compound and includes, but is not limited to, other solid state molecular forms including hydrates (e.g., bound water present in the crystalline structure) and solvates (e.g., bound solvents other than water) of the same compound.

The term "amorphous" refers to any solid substance which lacks order in three dimensions. In some instances, amorphous solids may be characterized by known techniques, including X-ray powder diffraction (PXRD) crystallography, solid state nuclear magnet resonance (ssNMR) spectroscopy, differential scanning calorimetry (DSC), or some combination of these techniques.

The term "crystalline" refers to any solid substance exhibiting three-dimensional order, which in contrast to an amorphous solid substance, gives a distinctive PXRD pattern with sharply defined peaks.

The term "solvate" describes a molecular complex comprising the drug substance and a stoichiometric or non-stoichiometric amount of one or more solvent molecules (e.g., ethanol). When the solvent is tightly bound to the drug the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex will often be non-stoichiometric.

The term "hydrate" describes a solvate comprising the drug substance and a stoichiometric or non-stoichiometric amount of water.

The term "powder X-ray diffraction pattern" or "PXRD pattern" refers to the experimentally observed diffractogram or parameters derived therefrom. Powder X-ray diffraction patterns are characterized by peak position (abscissa) and peak intensities (ordinate).

The term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific solid form is intended to mean the 2θ values (in degrees) as measured using the X-ray diffraction experimental conditions as described herein.

Solid Forms of the Compound of Formula I

The solid forms of the compound of Formula I disclosed herein can be characterized by one or more of the following: powder X-ray diffraction pattern (i.e., X-ray diffraction peaks at various diffraction angles (2θ)), solid state nuclear magnetic resonance (NMR) spectral pattern, Raman spectral diagram pattern, Infrared spectral pattern, aqueous solubility, light stability under International Conference on Harmonization (ICH) high intensity light conditions, and physical and chemical storage stability. For example, the solid forms of the compound of Formula I were each characterized by the positions and relative intensities of peaks in their powder X-ray diffraction patterns.

The powder X-ray diffraction patterns of the solid forms of the compound of Formula I were collected using a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector version 2.2b software. Data acquisition parameters were as shown in the Table 1 below.

TABLE 1

Data Acquisition Parameters for PXRD.

| | |
|---|---|
| Voltage | 45 kV |
| Amperage | 40 mA |
| Incident beam Soller slit (rad.) | 0.04 |
| Diffracted beam Soller slit (rad.) | 0.02 |
| Divergence slit | ½° |
| Step size | 0.017° 2θ |
| Scan range | 1-39.99° 2θ |
| Revolution time | 1.0 s |
| Scan speed | 3.2°/min (+/− 0.1°/min depending on sample) |
| Collection time | 720 s (+/−2 s depending on sample) |
| Temperature | Ambient |

More generally, to perform an X-ray diffraction measurement on a transmission instrument like the PANalytical system used for measurements reported herein, a specimen of the sample is sandwiched between 3-μm-thick films and analyzed in transmission geometry. The incident X-ray beam is directed at the sample, initially at a small angle relative to the plane of the holder, and then moved through an arc that continuously increases the angle between the incident beam and the plane of the holder. Measurement differences associated with such X-ray powder analyses result from a variety of factors including: (a) errors in sample preparation; (b) instrument errors; (c) calibration errors; (d) operator errors (including those errors present when determining the peak locations); and (e) the nature of the material (e.g., preferred orientation and transparency errors). Calibration errors and sample height errors often result in a shift of all the peaks in the same direction. These shifts can be identified from the X-ray diffractogram and can be eliminated by compensating for the shift (applying a systematic correction factor to all peak position values) or recalibrating the instrument. In general, this correction factor will bring the measured peak positions into agreement with the expected peak positions and may be in the range ±0.2° 2θ

One skilled in the art will appreciate that the peak positions (2θ) will show some inter-apparatus variability, typically ±0.2° 2θ. Accordingly, where peak positions (2θ) are reported, one skilled in the art will recognize that such numbers are intended to encompass such inter-apparatus variability. Furthermore, where the crystalline forms of the present invention are described as having a powder X-ray diffraction peak position essentially the same as that shown in a given figure, the term "essentially the same" is also intended to encompass such inter-apparatus variability in diffraction peak positions. Further, one skilled in the art will appreciate that relative peak intensities will show inter-apparatus variability as well as variability due to the degree of crystallinity, preferred orientation, prepared sample surface, and other factors known to those skilled in the art, and should be taken as qualitative measures only.

PXRD peak Identification was performed as follows. A PXRD pattern was analyzed for Form 1 and Form 4; preferred orientation and particle statistic effects were not assessed. Under most circumstances, peaks within the range of up to about 30° 2θ were selected. Peaks with an intensity greater than or equal to 2% of the most intense peak were used for peak selection. Peak positions were rounded to the nearest 0.1° 2θ. The location of the peaks along the x-axis (° 2θ) was determined using TRIADS™ v2.0 software; the TRIADS™ algorithm is described by U.S. Pat. No. 8,576, 985, which is hereby incorporated by reference in its entirety. As noted above, peak position variabilities are given to within ±0.2° 2θ based upon recommendations outlined in the USP discussion of variability in x-ray powder diffraction (see United States Pharmacopeia, USP 37, NF 32, through S1 <941>, 503, May 1, 2014).

The solid forms of the compound of Formula I can also be characterized Raman spectroscopy. Raman spectra were collected using NXR FT-Raman module interfaced to a Nexus 670 FT-IR spectrophotometer (Thermo Nicolet), equipped with an InGaAs detector. Wavelength verification was performed using sulfur and cyclohexane. Each sample was prepared for analysis by packing the sample material into a pellet holder. Approximately 0.5 W of Nd:YVO4 laser power (1064 nm excitation wavelength) was used to irradiate each sample. Each spectrum represents 256 co-added scans collected at a spectral resolution of 2 cm-1, obtained at ambient temperature. Peak positions were picked at the peak maxima. Relative intensity values were classified as strong (S), medium (M) and weak (W) using the following criteria: strong (1.00-0.75); medium (0.74-0.30) and weak (0.29 and below).

The solid forms of the compound of Formula I can also be characterized using solid state NMR spectroscopy. The 13C solid state spectra for the solid forms of Formula 1 were collected as follows. Solid State NMR (ssNMR) analysis was conducted at ambient temperature and pressure on a Bruker-Biospin CPMAS probe positioned into a Bruker-Biospin Avance III 500 MHz (1H frequency) NMR spectrometer. The packed rotor was oriented at the magic angle and spun at 15.0 kHz. The carbon ssNMR spectra were collected at ambient temperature using a proton decoupled cross-polarization magic angle spinning (CPMAS) experiment. A phase modulated proton decoupling field of 80-100 kHz was applied during spectral acquisition. The cross-polarization contact time was set to 2.0 ms. The recycle delay was set to 180 seconds for Form 1, 50 seconds for Form 4 and 5 seconds for Form 6. The number of scans was adjusted to obtain an adequate signal noise ratio. The carbon spectra were referenced using an external standard of crystalline adamantane, setting its upfield resonance to 29.5 ppm (as determined from neat tetramethylsilane). Automatic peak picking was performed using Bruker-BioSpin TopSpin version 3.1 software. Generally, a threshold value of 5% relative intensity was used to preliminary select peaks. The output of the automated peak picking was visually checked to ensure validity and adjustments manually made if necessary. Although specific 13C solid state NMR peak values are reported herein there does exist a range for these peak values due to differences in instruments, samples, and sample preparation. This is common practice in the art of solid state NMR because of the variation inherent in peak values. A typical variability for a 13C chemical shift x-axis value is on the order of plus or minus 0.2 ppm for a crystalline solid. The solid state NMR peak heights reported herein are relative intensities. Solid state NMR intensities can vary depending on the actual setup of the CPMAS experimental parameters and the thermal history of the sample.

One of skill in the art will also recognize that crystalline forms of a given compound can exist in substantially pure forms of a single polymorph, but can also exist in a crystalline form that comprises two or more different polymorphs or amorphous forms. Where a solid form comprises two or more polymorphs, the X-ray diffraction pattern will have peaks characteristic of each of the individual polymorphs of the present invention. For example, a solid form that comprises two polymorphs will have a powder X-ray diffraction pattern that is a convolution of the two X-ray diffraction patterns that correspond to the substantially pure solid forms. For example, a solid form of the compound for Formula I can contain a first and second solid form where the solid form contains at least 10% by weight of the first form. In a further example, the solid form contains at least 20% by weight of the first form. Even further examples contain at least 30%, at least 40%, or at least 50% by weight of the first form. One of skill in the art will recognize that many such combinations of several individual forms in varying amounts are possible.

Form 1

Form 1 is a crystalline, non-hygroscopic, anhydrous, form of a compound of Formula I that can be produced as described in Example 1.

Form 1 was characterized by the PXRD pattern shown in FIG. 1, which was measured on a PANalytical X'Pert PRO MPD using an incident beam of Cu radiation produced using an Optix long, fine-focus source. The PXRD pattern of Form 1, expressed in terms of the degree (2θ) and relative intensities with a relative intensity of ≥2.0%, is shown in FIG. 2. The relative intensities may change depending on the crystal size and morphology.

Form 1 has been characterized herein as a neat substance to identify Form 1 characteristic peaks using appropriate analytical methods. These analytical methods result in peak values that are characteristic of Form 1, having a defined range within an accepted variability. However, the relative intensity of these characteristic peaks are expected to change once Form 1 is mixed with any additional components, such as those utilized in a formulation. It is thus understood by one skilled in the art of instrumental analysis that the analytical parameters of a specific method may require additional optimization to enable for the detection of these characteristic peaks once it is mixed and diluted with additional components within a drug product formulation. For example, as described in the following paragraph, PXRD method can be further optimized to enable detection of characteristic Form 1 peaks if Form 1 were to be mixed with additional components. One skilled in the art of PXRD analysis would understand that the peak values associated with the Form 1 characteristic peaks would not be altered as a result of this method optimization.

Figure 21:
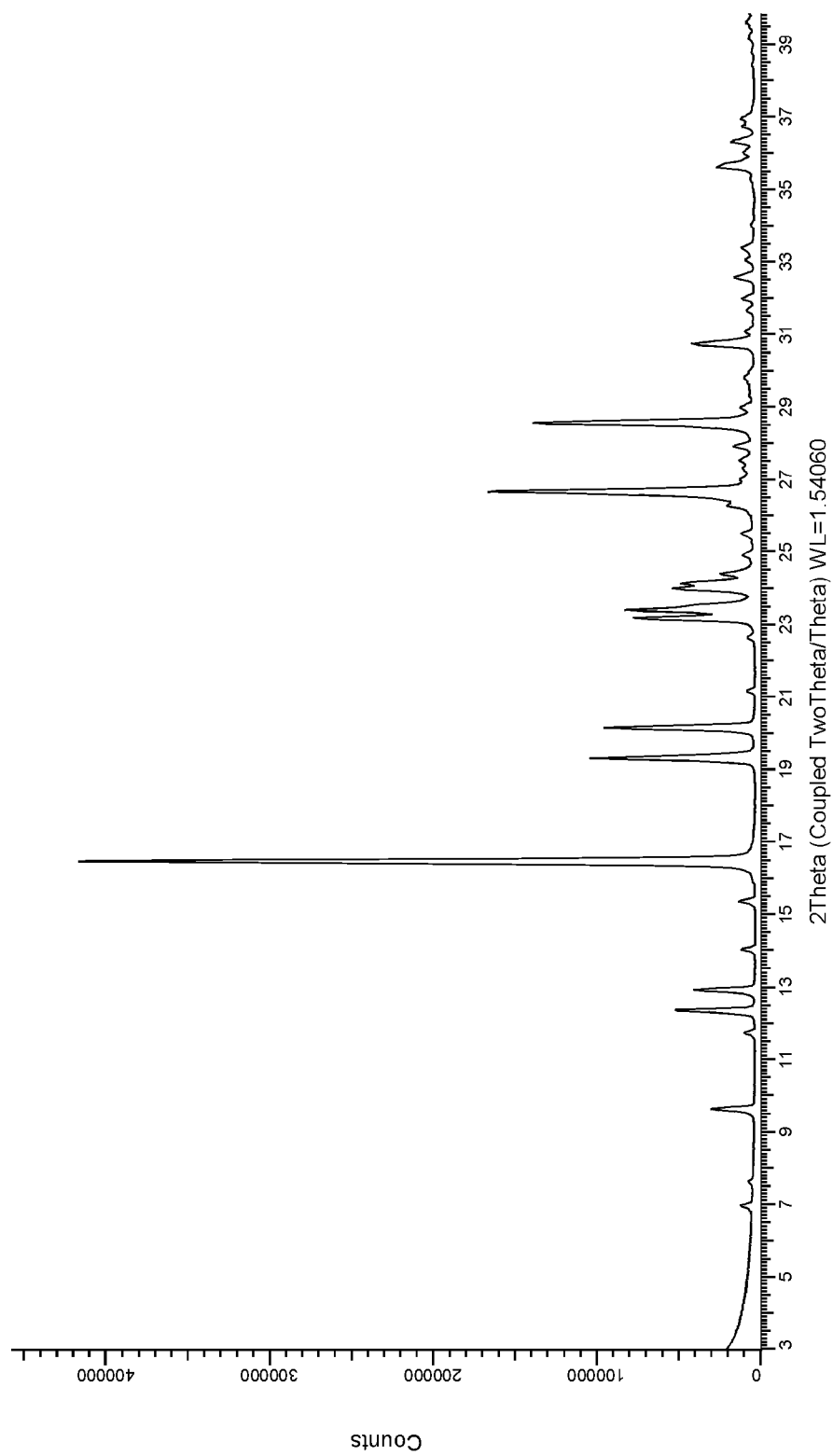
FIG. 21 depicts a characteristic PXRD pattern of Form 1 carried out on a Bruker AXS D8 ADVANCE diffractometer.

Powder X-ray diffraction analysis for Form 1 was also conducted using a Bruker AXS D8 ADVANCE diffractometer equipped with a Cu radiation source (K-α average). The system is equipped with a 2.5 axial Soller slits on the primary side. The secondary side utilizes 2.5 axial Soller slits and motorized slits. Diffracted radiation was detected by a Lynx Eye XE detector. The X-ray tube voltage and amperage were set to 40 kV and 40 mA respectively. Data was collected in the Theta-Theta goniometer at the Cu wavelength from 3.0 to 40.0 degrees 2-Theta using a step size of 0.037 degrees and a step time of 10 seconds. Samples were prepared by placing them in a low background holder and rotated during collection. The resulting Form 1 powder pattern is given in FIG. 21.

Figure 5:
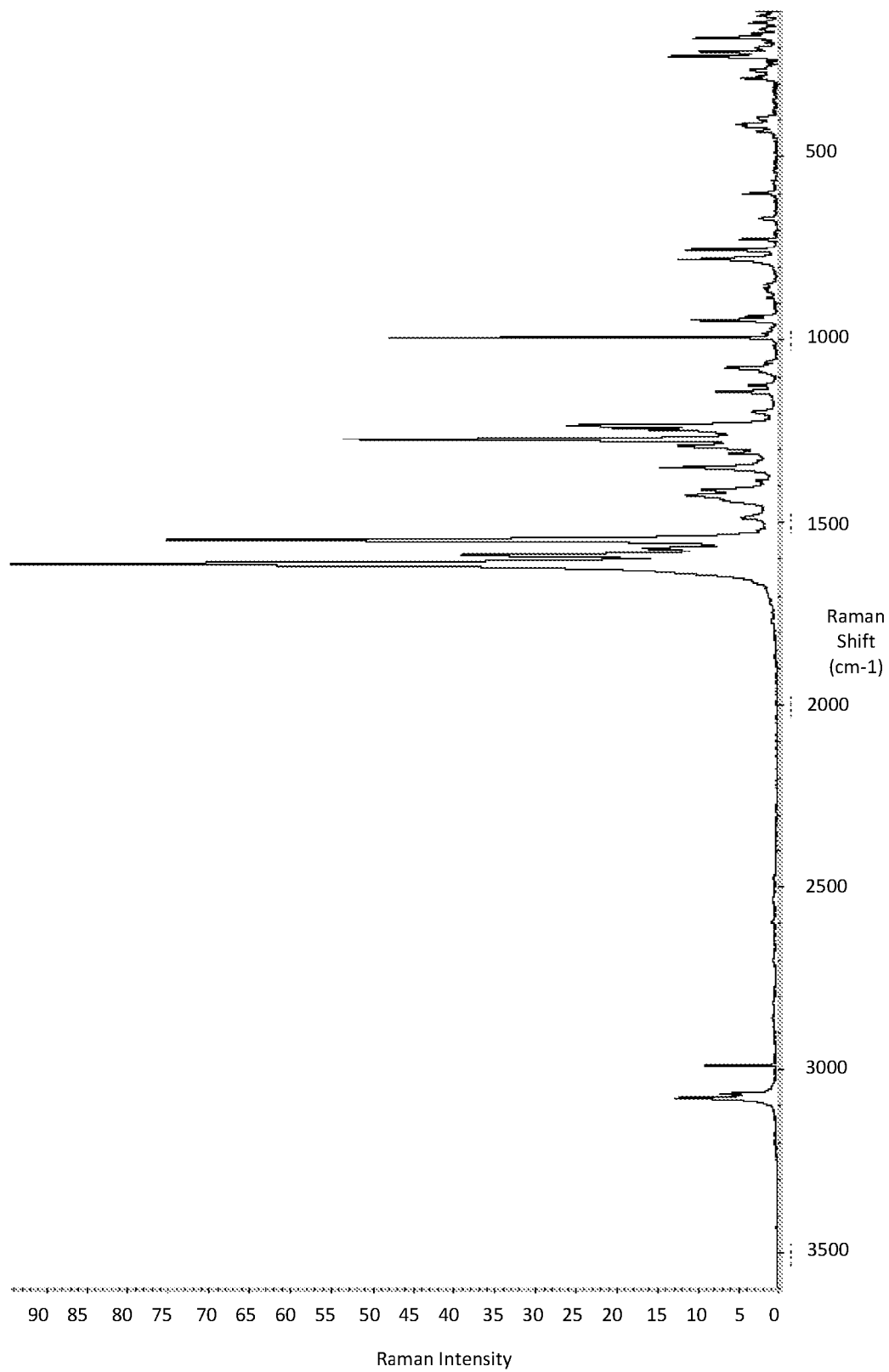
FIG. 5 depicts a characteristic Raman spectrum of Form 1 carried out on a NXR FT-Raman module interfaced to a Nexus 670 FT-IR spectrophotometer (Thermo Nicolet), equipped with an InGaAs detector.

Form 1 was also characterized by the Raman spectral pattern shown in FIG. 5, which was carried out on a NXR FT-Raman module interfaced to a Nexus 670 FT-IR spectrophotometer (Thermo Nicolet), equipped with an InGaAs detector. The Raman spectral peaks of Form 1 are shown in FIG. 6.

Figure 9:
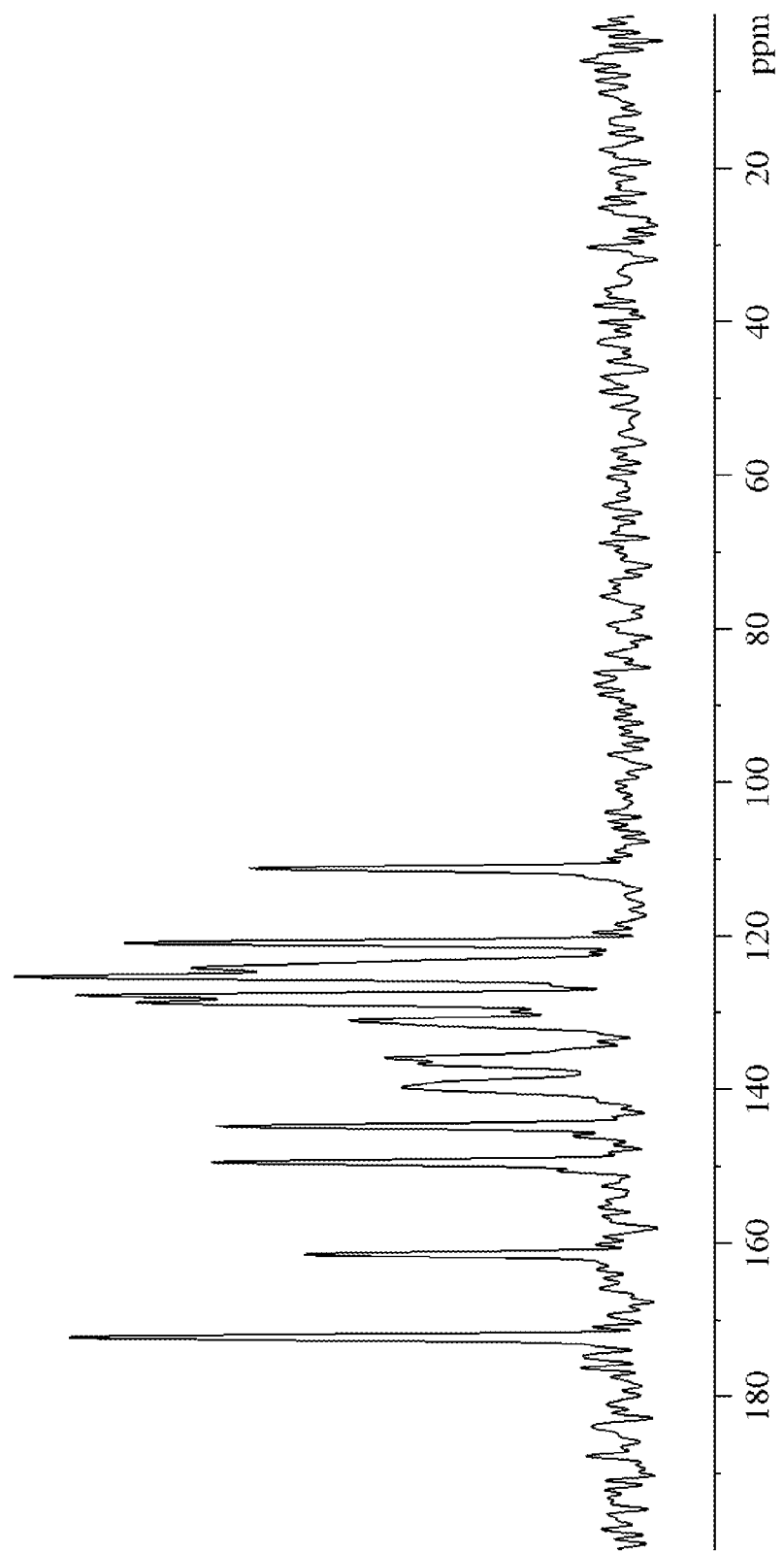
FIG. 9 depicts a characteristic 13C solid state NMR spectrum of Form 1 carried out on a Bruker-Biospin 4 mm CPMAS probe positioned into a Bruker-Biospin Avance III 500 MHz NMR spectrometer.

Form 1 was also characterized by the solid state NMR spectral pattern shown in FIG. 9, which was carried out on a Bruker-Biospin 4 mm CPMAS probe positioned into a Bruker-Biospin Avance III 500 MHz NMR spectrometer. The 13C chemical shifts of Form 1 are shown in FIG. 10.

Form 1 was analyzed via isothermal vapor sorption analysis, which is a gravimetric technique that measures how quickly and how much of a solvent is absorbed by a sample: such as a dry powder absorbing water. It does this by varying the vapor concentration surrounding the sample and measuring the change in mass which this produces. The isothermal vapor sorption analysis of Form 1 shows that Form 1 is anhydrous with a less than 0.25% reversible weight gain at up to 90% relative humidity at ambient temperature.

Form 4

Form 4 is a crystalline, non-hygroscopic, anhydrous, form of the compound of Formula I that can be produced as described in Example 2.

Figure 3:
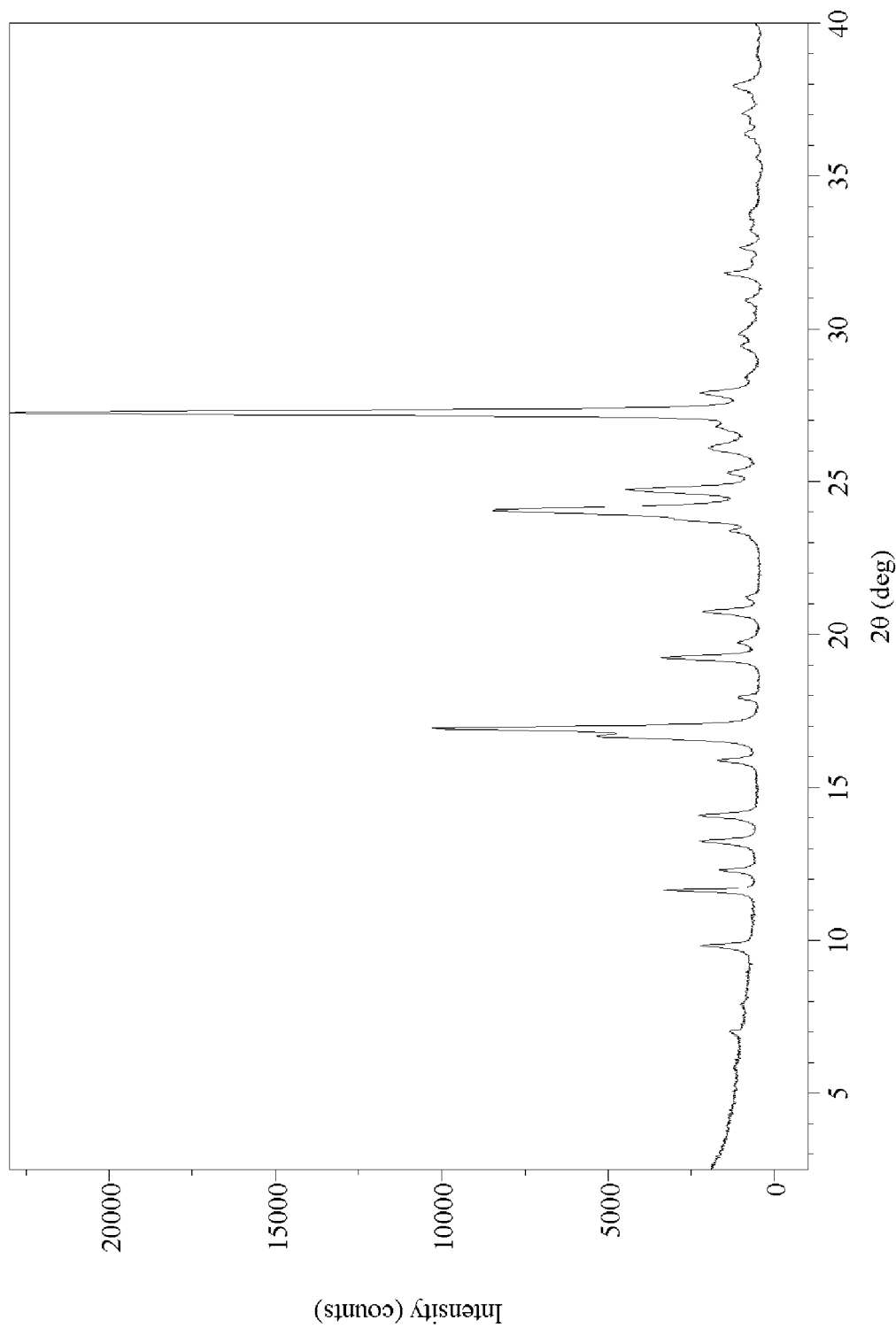
FIG. 3 depicts a characteristic PXRD pattern of Form 4 carried out on a PANalytical X'Pert PRO MPD diffractometer.

Form 4 was characterized by the PXRD pattern shown in FIG. 3, which was measured on a PANalytical X'Pert PRO MPD using an incident beam of Cu radiation produced using an Optix long, fine-focus source. The PXRD pattern of Form 4, expressed in terms of the degree (2θ) and relative intensities with a relative intensity of ≥2.0%, is shown in FIG. 4. The relative intensities may change depending on the crystal size and morphology.

Figure 7:
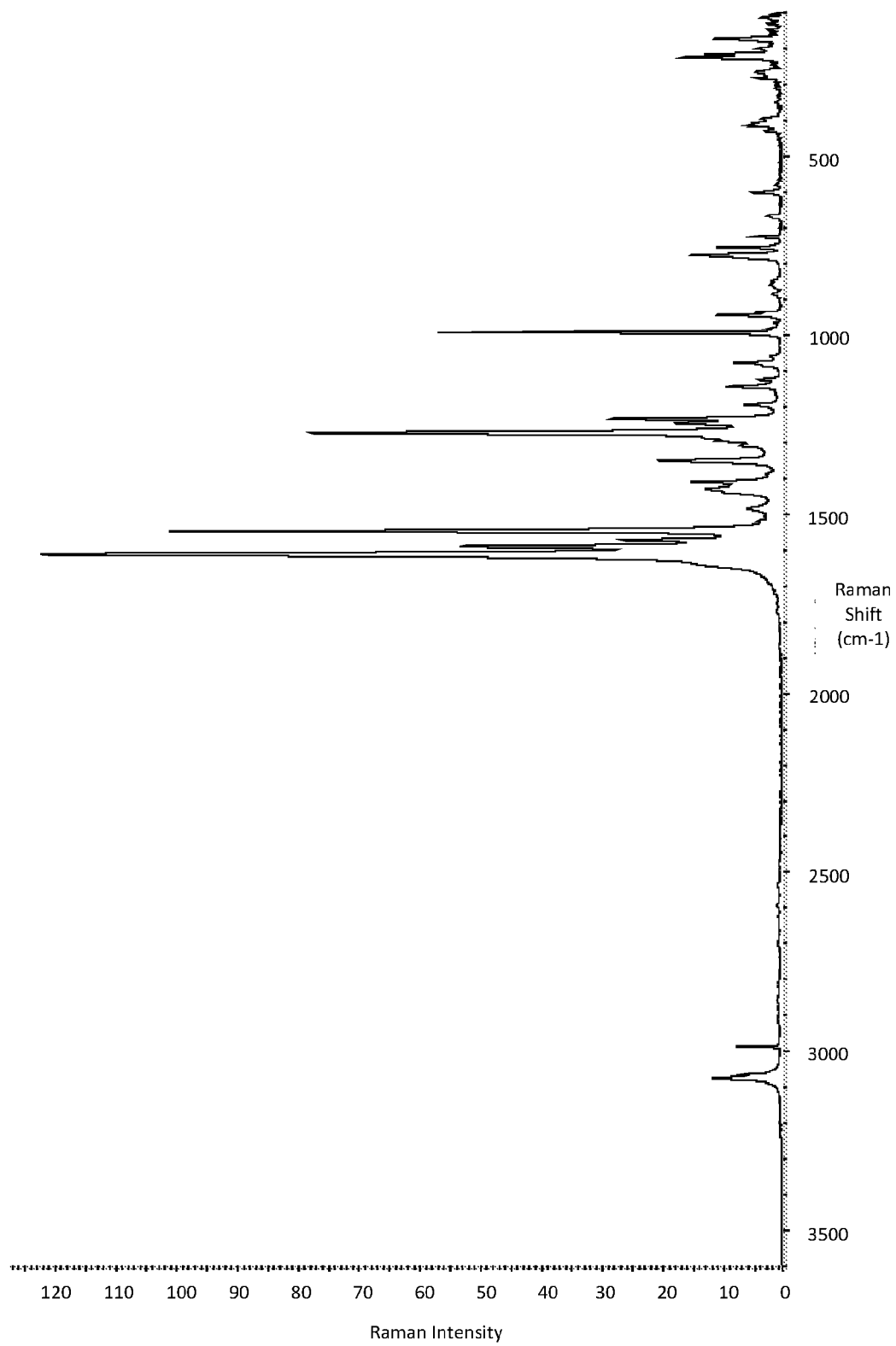
FIG. 7 depicts a characteristic Raman spectrum of Form 4 carried out on a NXR FT-Raman module interfaced to a Nexus 670 FT-IR spectrophotometer (Thermo Nicolet), equipped with an InGaAs detector.

Form 4 was also characterized by the Raman spectral pattern shown in FIG. 7, which was carried out on a NXR FT-Raman module interfaced to a Nexus 670 FT-IR spectrophotometer (Thermo Nicolet), equipped with an InGaAs detector. The Raman spectral peaks of Form 4 are shown in FIG. 8.

Figure 11:
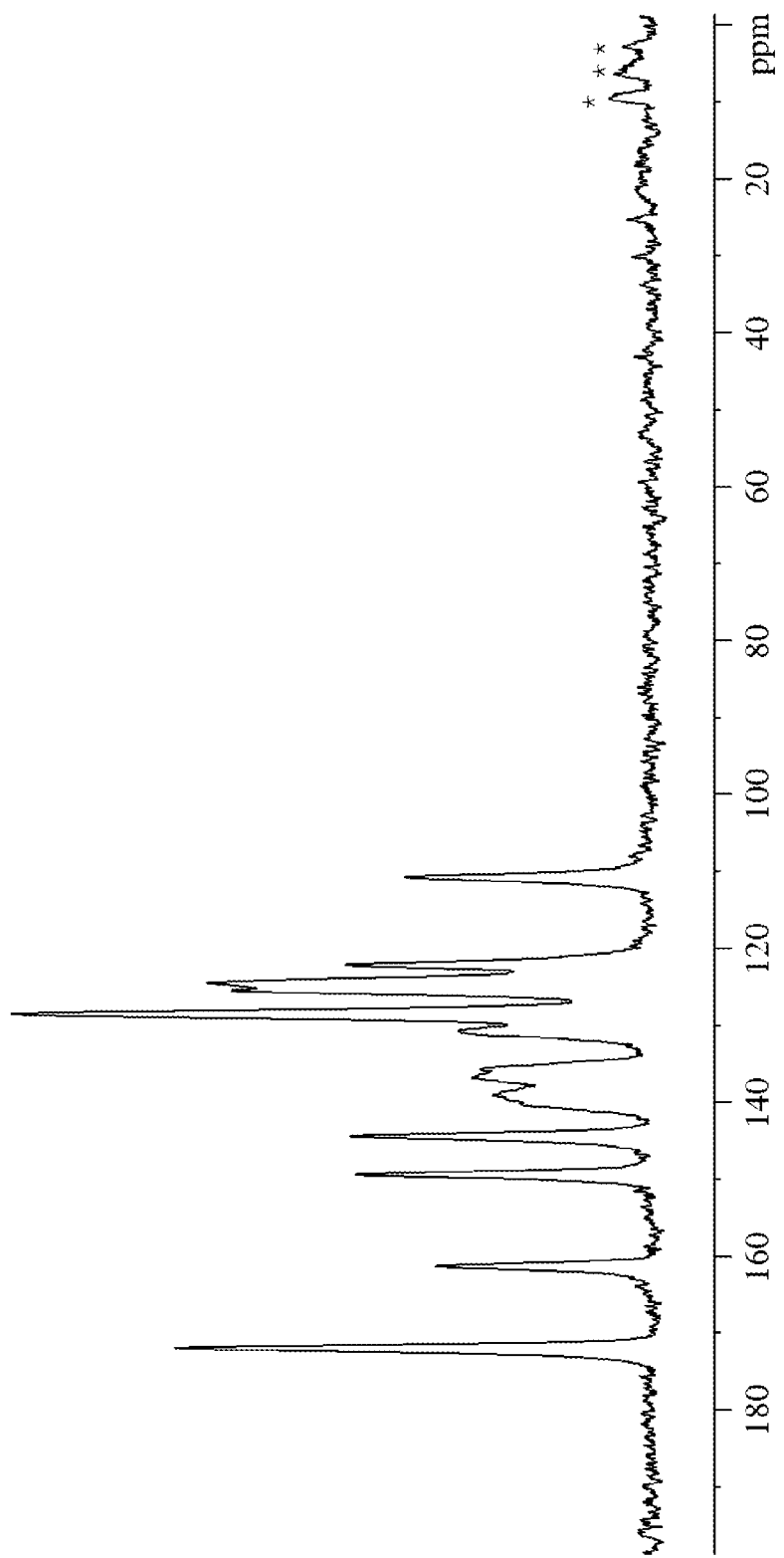
FIG. 11 depicts a characteristic 13C solid state NMR spectrum of Form 4 carried out on a Bruker-Biospin 4 mm CPMAS probe positioned into a Bruker-Biospin Avance III 500 MHz NMR spectrometer collected under 15.0 kHz of magic angle spinning. The peaks marked by asterisks are spinning sidebands.

Form 4 was also characterized by the solid state NMR spectral pattern shown in FIG. 11, which was carried out on a Bruker-Biospin 4 mm CPMAS probe positioned into a Bruker-Biospin Avance III 500 MHz NMR spectrometer. The 13C chemical shifts of Form 4 are shown in FIG. 12.

Form 2

Form 2 is crystalline THF solvate of the compound of Formula I that can be produced as described in Example 3.

Figure 13:
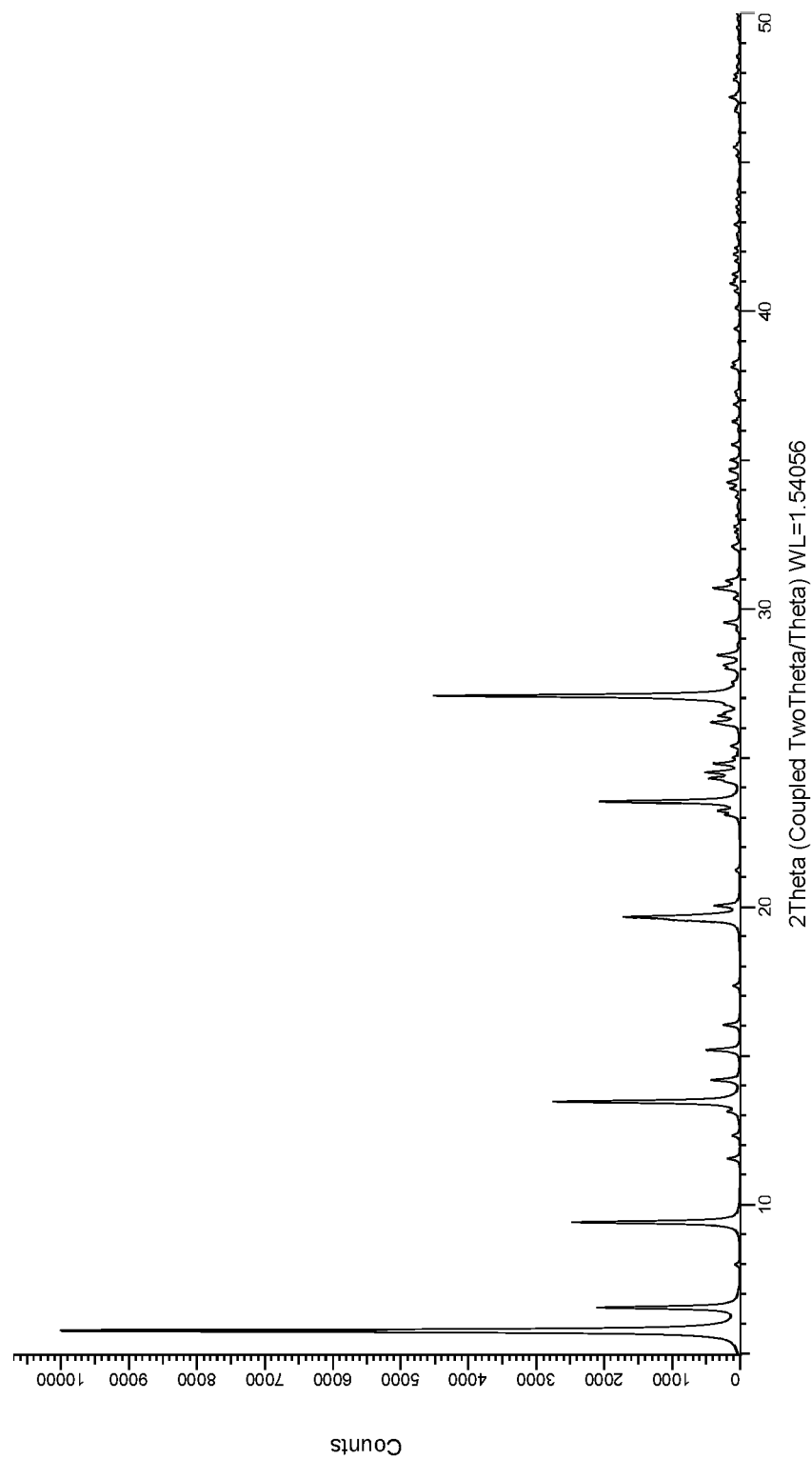
FIG. 13 depicts the calculated powder x-ray pattern of Form 2.

The calculated powder pattern of Form 2 shown in FIG. 13 was prepared using Mercury v. 3.1 (http://www.ccdc.cam.ac.uk/mercury/).

Form 6

Form 6 is a crystalline, non-hygroscopic, anhydrous, form of the compound of Formula I that can be produced as described in Example 4.

Figure 14:
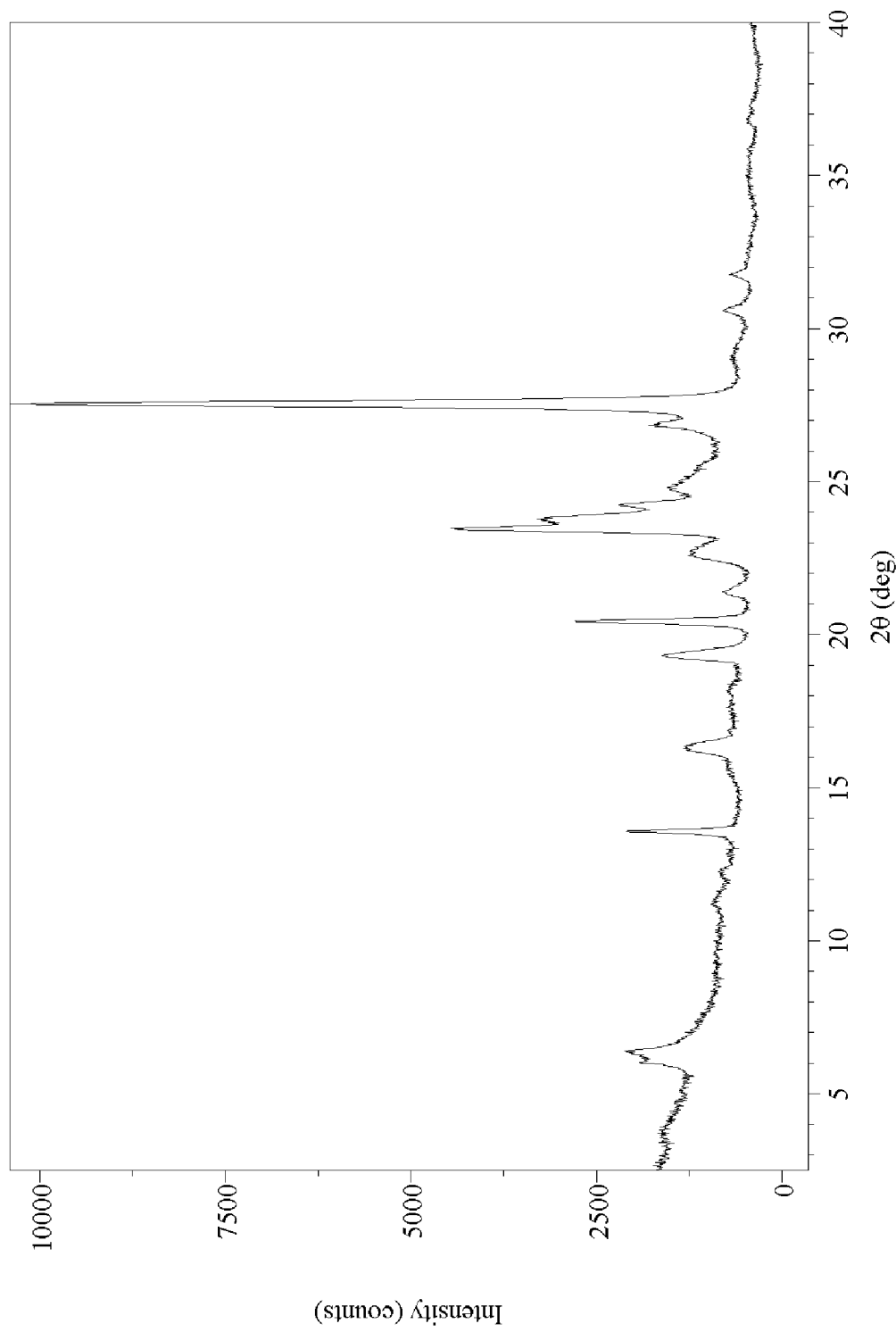
FIG. 14 depicts a characteristic PXRD pattern of Form 6 carried out on a PANalytical X'Pert PRO MPD diffractometer.

Form 6 was characterized by the PXRD pattern shown in FIG. 14, which was measured on a PANalytical X'Pert PRO MPD using an incident beam of Cu radiation produced using an Optix long, fine-focus source. The PXRD pattern of Form 6, expressed in terms of the degree (2θ) and relative intensities with a relative intensity of ≥2.0%, is shown in FIG. 15. The relative intensities may change depending on the crystal size and morphology.

Figure 16:
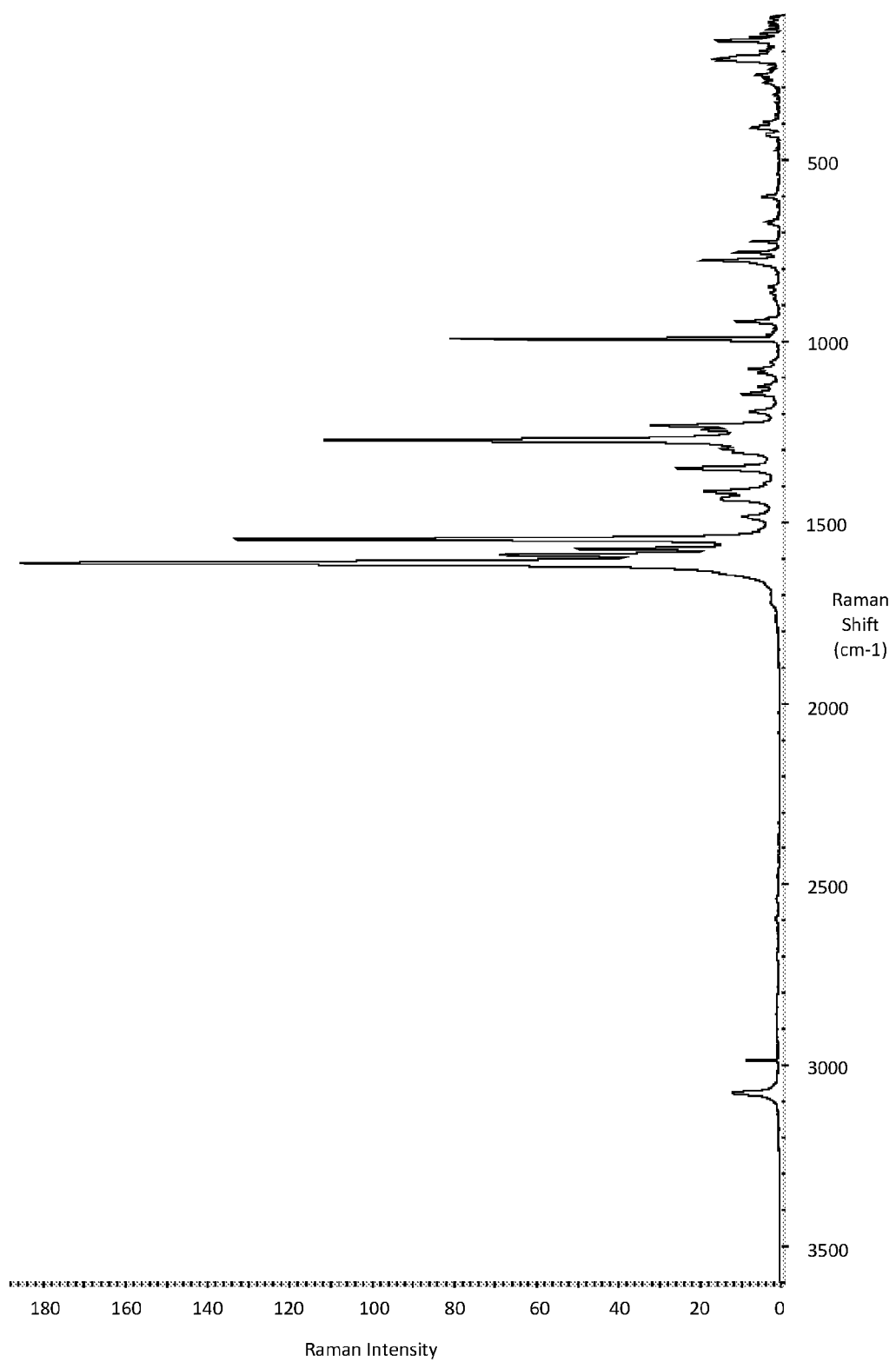
FIG. 16 depicts a characteristic Raman spectrum of Form 6 carried out on a NXR FT-Raman module interfaced to a Nexus 670 FT-IR spectrophotometer (Thermo Nicolet), equipped with an InGaAs detector.

Form 6 was also characterized by the Raman spectral pattern shown in FIG. 16, which was carried out on a NXR FT-Raman module interfaced to a Nexus 670 FT-IR spectrophotometer (Thermo Nicolet), equipped with an InGaAs detector. The Raman spectral peaks of Form 6 are shown in FIG. 17.

Figure 18:
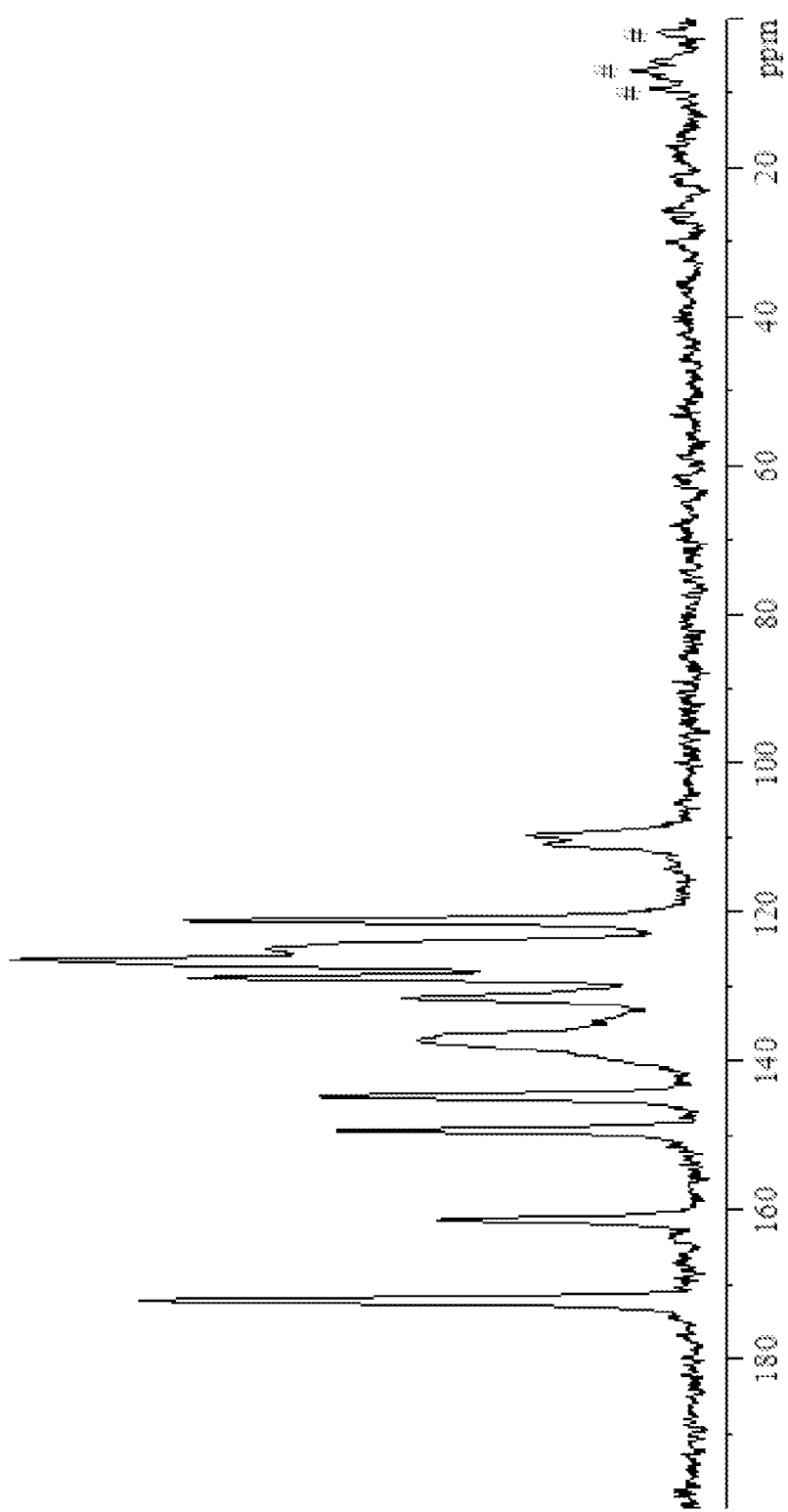
FIG. 18 depicts a characteristic 13C solid state NMR spectrum of Form 6 carried out on a Bruker-Biospin 4 mm CPMAS probe positioned into a Bruker-Biospin Avance III 500 MHz NMR spectrometer collected under 15.0 kHz of magic angle spinning. The peaks marked by hashed marks are spinning sidebands.
Figure 20:
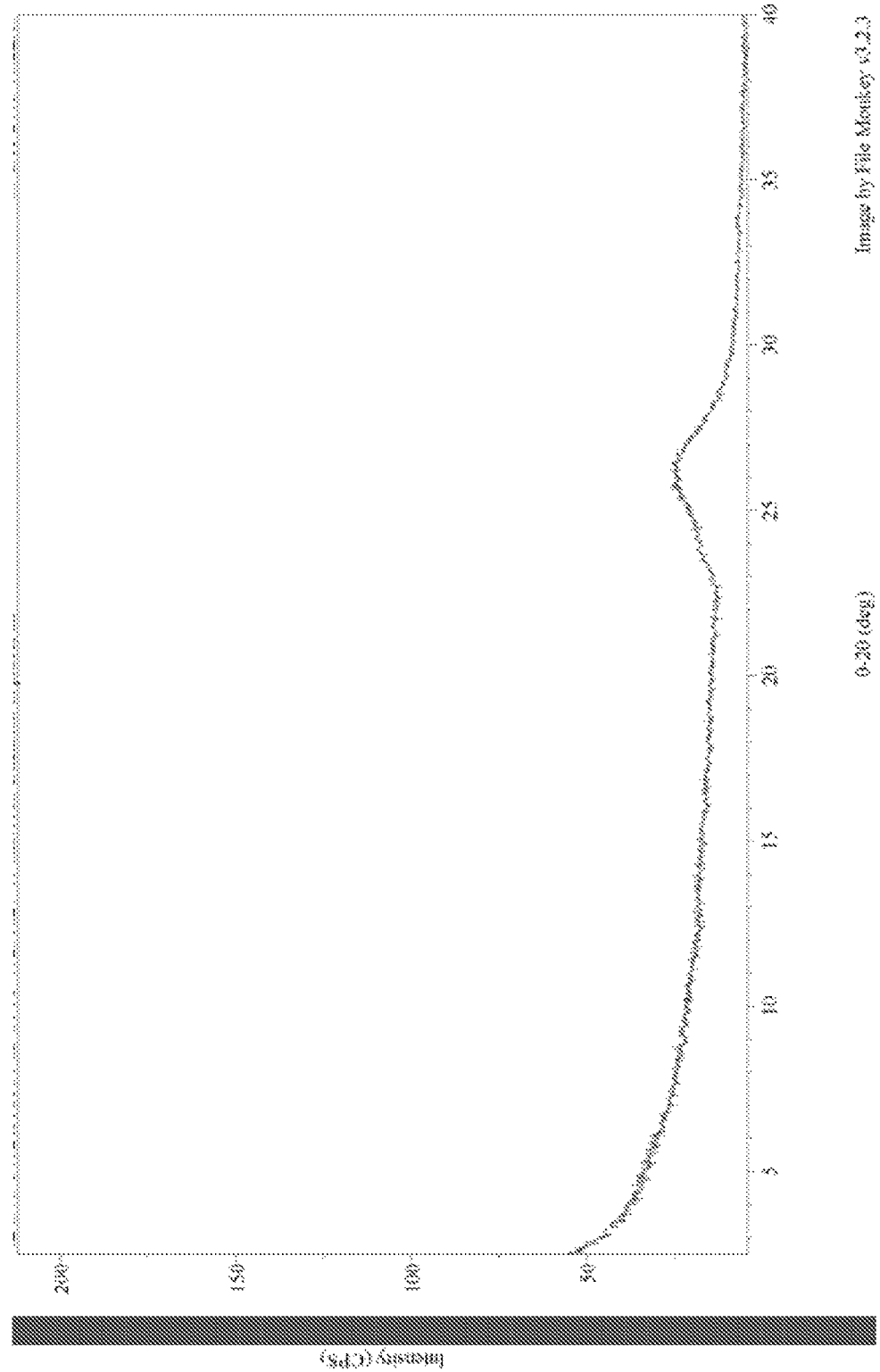
FIG. 20 depicts a characteristic PXRD pattern of the amorphous form of 6-carboxy-2-(3,5-dichlorophenyl)-benzoxazole carried out on a PANalytical X'Pert PRO MPD diffractometer.

Form 6 was also characterized by the solid state NMR spectral pattern shown in FIG. 18, which was carried out on a Bruker-Biospin 4 mm CPMAS probe positioned into a Bruker-Biospin Avance III 500 MHz NMR spectrometer. The 13C chemical shifts of Form 6 are shown in FIG. 19.

Pharmaceutical Compositions

The active agents (i.e., the solid forms of compound of Formula I described herein) of the invention may be formulated into pharmaceutical compositions suitable for mammalian medical use. Any suitable route of administration may be employed for providing a patient with an effective dosage of any of the solid forms of compound of Formula I described herein. For example, peroral or parenteral formulations and the like may be employed. Dosage forms include capsules, tablets, dispersions, suspensions and the like, e.g. enteric-coated capsules and/or tablets, capsules and/or tablets containing enteric-coated pellets of the solid forms of compound of Formula I described herein. In all dosage forms, the solid forms of compound of Formula I described herein can be admixed with other suitable constituents. The compositions may be conveniently presented in unit dosage forms, and prepared by any methods known in the pharmaceutical arts. Pharmaceutical compositions of the invention comprise a therapeutically effective amount of the active agent and one or more inert, pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20™" and "TWEEN 80™", and Pluronic® F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in Remington: The Science & Practice of Pharmacy, 19th ed., Williams & Williams, (1995), and in the "Physician's Desk Reference", 52nd ed., Medical Economics, Montvale, N.J. (1998), and in "Handbook of Pharmaceutical Excipients", 3rd. Ed., Ed. A. H. Kibbe, Pharmaceutical Press, 2000. The active agents of the invention may be formulated in compositions including those suitable for oral, rectal, topical, nasal, ophthalmic, or parenteral (including intraperitoneal, intravenous, subcutaneous, or intramuscular injection) administration.

The amount of the active agent in the formulation will vary depending upon a variety of factors, including dosage form, the condition to be treated, target patient population, and other considerations, and will generally be readily determined by one skilled in the art. A therapeutically effective amount will be an amount necessary to inhibit transthyretin (TTR) dissociation (i.e. prevents dissociation of the native TTR tetramer into monomers). Compositions will generally contain anywhere from about 0.001% by weight to about 99% by weight active agent, preferably from about 0.01% to about 5% by weight active agent, and more preferably from about 0.01% to 2% by weight active agent, and will also depend upon the relative amounts of excipients/additives contained in the composition.

A pharmaceutical composition of the invention is administered in conventional dosage form prepared by combining a therapeutically effective amount of an active agent as an active ingredient with one or more appropriate pharmaceutical carriers according to conventional procedures. These procedures may involve mixing granulating and compressing or dissolving the ingredients as appropriate to the desired preparation.

The pharmaceutical carrier(s) employed may be either solid or liquid. Exemplary solid carriers include lactose, sucrose, talc, gelatin, agar, pectin, acacia, magnesium stearate, stearic acid and the like. Exemplary liquid carriers include syrup, peanut oil, olive oil, water and the like. Similarly, the carrier(s) may include time-delay or time release materials known in the art, such as glyceryl monostearate or glyceryl distearate alone or with a wax, ethylcellulose, hydroxypropylmethyl-cellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

It will be appreciated that the actual dosages of the solid forms of compound of Formula I described herein used in the compositions of this invention will vary according to the particular solid form being used, the particular composition formulated, the mode of administration and the particular site, host and disease being treated. Those skilled in the art using conventional dosage-determination tests in view of the experimental data for an agent can ascertain optimal dosages for a given set of conditions. For oral administration, an exemplary daily dose generally employed is from about 0.001 to about 1000 mg/kg of body weight, more preferably from about 0.001 to about 50 mg/kg body weight, with courses of treatment repeated at appropriate intervals. Administration of prodrugs is typically dosed at weight levels that are chemically equivalent to the weight levels of the fully active form. In the practice of the invention, the most suitable route of administration as well as the magnitude of a therapeutic dose will depend on the nature and severity of the disease to be treated. The dose, and dose frequency, may also vary according to the age, body weight, and response of the individual patient. In general, a suitable oral dosage form may cover a dose range from 0.5 mg to 100 mg of active ingredient total daily dose, administered in one single dose or equally divided doses. A preferred amount of the solid forms of compound of Formula I described herein in such formulations is from about 0.5 mg to about 20 mg, such as from about 1 mg to about 10 mg or from about 1 mg to about 5 mg.

The compositions of the invention may be manufactured in manners generally known for preparing pharmaceutical compositions, e.g., using conventional techniques such as mixing, dissolving, granulating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations that can be used pharmaceutically.

For oral administration, the solid forms of compound of Formula I described herein can be formulated by combining the active agent with pharmaceutically acceptable carriers known in the art. Such carriers enable the compounds of the invention to be formulated as tablets, pills, capsules, gels, syrups, slurries, suspensions and the like, for oral ingestion by a patient to be treated. Pharmaceutical preparations for oral use can be obtained using a solid excipient in admixture with the active agent, optionally grinding the resulting mixture, and processing the mixture of granules after adding suitable auxiliaries. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration to the eye, the solid forms of compound of Formula I described herein may be delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and sclera. The pharmaceutically acceptable ophthalmic vehicle may be, for example, an ointment, vegetable oil, or an encapsulating material. An active agent of the invention may also be injected directly into the vitreous and aqueous humor or subtenon.

Alternatively, the active ingredient may be in powder form for constitution with a suitable vehicle, e.g., sterile pyrogen-free water, before use. The solid forms of compound of Formula I described herein may also be formulated in rectal or vaginal compositions such as suppositories or retention enemas, e.g., containing conventional suppository bases such as cocoa butter or other glycerides.

In addition to the formulations described above, the solid forms may also be formulated as a depot preparation. Such long-acting formulations may be administered by implantation (for example, subcutaneously or intramuscularly) or by intramuscular injection. Thus, for example, the solid forms may be formulated with suitable polymeric or hydrophobic materials (for example, as an emulsion in an acceptable oil) or ion-exchange resins, or as sparingly soluble derivatives, for example, as a sparingly soluble salt.

Additionally, the solid forms of compound of Formula I described herein may be delivered using a sustained-release system, such as semi-permeable matrices of solid hydrophobic polymers containing the therapeutic agent. Various sustained-release materials have been established and are known by those skilled in the art.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

In certain embodiments, the invention relates to any of the aforementioned pharmaceutical compositions, wherein said solid form is Form 1. In certain embodiments, the invention relates to any of the aforementioned pharmaceutical compositions, wherein said solid form is Form 4.

Articles of Manufacture

The solid forms of compound of Formula I described herein may be packaged as articles of manufacture containing packaging material, a solid form of the compound of Formula I as provided herein, which is effective for modulating TTR folding, or for treatment, prevention or amelioration of one or more symptoms of TTR mediated diseases or disorders, or diseases or disorders in which TTR misfolding, is implicated, within the packaging material, and a label that indicates that the solid form is used for modulating TTR folding, or for treatment, prevention or amelioration of one or more symptoms of TTR mediated diseases or disorders, or diseases or disorders in which TTR misfolding is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment, including a variety of treatments for any disease or disorder in which TTR misfolding is implicated as a mediator or contributor to the symptoms or cause.

In certain embodiments, the invention relates to any of the aforementioned articles of manufacture, wherein said solid form is Form 1. In certain embodiments, the invention relates to any of the aforementioned articles of manufacture, wherein said solid form is Form 2. In certain embodiments, the invention relates to any of the aforementioned articles of manufacture, wherein said solid form is Form 4. In certain embodiments, the invention relates to any of the aforementioned articles of manufacture, wherein said solid form is Form 6.

In Vitro Biological Testing

A number of in vitro tests can be used to evaluate the solid forms for their ability to stabilize transthyretin tetramers or prevent formation of fibrils. The tests can include a fibril formation assay, a plasma selectivity assay, determination of the three-dimensional structure of a transthyretin compound complex (e. g. by X-ray crystallography), kinetics of transthyretin tetramer dissociation or fibril formations, and determining the stoichiometry and energetics of transthyretin compound interactions, by, for example, centrifugation or calorimetry. Details of exemplary in vitro assays are provided in U.S. Pat. No. 7,214,695 (which is hereby incorporated by reference in it entirety).

Methods of Using the Solid Forms of the Invention

The compound of Formula I described herein is useful for stabilizing the protein transthyretin (TTR), dissociation of which is implicated in TTR amyloidosis (i.e., prevents dissociation of the native TTR tetramer into monomers, which results in the inhibition of TTR amyloid fibril formation), thus providing treatments for transthyretin amyloid diseases in mammals, including humans.

At least some amyloid diseases appear to be caused by the deposition of any one of more than 20 nonhomologous proteins or protein fragments, ultimately affording a fibrillar cross-$\beta$-sheet quaternary structure. Formation of amyloid fibrils from a normally folded protein like transthyretin requires protein misfolding to produce an assembly-competent intermediate. The process of transthyretin (TTR) amyloidogenesis appears to cause senile systemic amyloidosis (SSA), familial amyloid polyneuropathy (FAP) and familial amyloid cardiomyopathy (FAC). SSA is associated with the deposition of wild-type TTR, while FAP and FAC are caused by the amyloidogenesis of one of over 80 TTR variants. See, for example, Colon, W.; Kelly, J. W. Biochemistry 1992, 31, 8654-60; Kelly, J. W. *Curr. Opin. Struct. Biol.* 1996, 6, 11-7; Liu, K.; et al. *Nat. Struct. Biol.* 2000, 7, 754-7; Westermark, P.; et al. *Proc. Natl. Acad. Sci. U.S.A* 1990, 87, 2843-5; Saraiva, M. J.; et al. *J. Clin. Invest.* 1985, 76, 2171-7; Jacobson, D. R.; et al. *N. Engl. J. Med.* 1997, 336, 466-73; Buxbaum, J. N.; Tagoe, C. E. *Ann. Rev. Med.* 2000, 51, 543-569; and Saraiva, M. *J. Hum. Mutat.* 1995, 5, 191-6, each of which is incorporated by reference in its entirety. Additional TTR amyloid diseases include cardiac amyloidosis following liver transplantation, peripheral nerve amyloidosis following liver transplantation, leptomeningeal amyloidosis, transthyretin mutant-associated carpal tunnel syndrome, vitreous deposition, and transthyretin mutant-associated skin amyloidosis.

Therapeutically effective amounts of the compound of Formula 1 may be administered, typically in the form of a pharmaceutical composition, to treat diseases mediated by modulation or regulation of TTR dissociation. An "effective amount" is intended to mean that amount of an agent that, when administered to a mammal in need of such treatment, is sufficient to effect treatment for a disease mediated by TTR dissociation. Thus, a therapeutically effective amount of Compound 1 is a quantity sufficient to modulate, regulate, or inhibit the dissociation of TTR such that a disease condition that is mediated by that activity is reduced or alleviated. "Treating" is intended to mean at least the mitigation of a disease condition in a mammal, such as a human, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition. Exemplary disease conditions include senile systemic amyloidosis (SSA), familial amyloid polyneuropathy (FAP), familial amyloid cardiomyopathy (FAC), cardiac amyloidosis following liver transplantation, peripheral nerve amyloidosis following liver transplantation, leptomeningeal amyloidosis, transthyretin mutant-associated carpal tunnel syndrome, vitreous deposition, and transthyretin mutant-associated skin amyloidosis.

EXAMPLES

The examples which follow will illustrate the preparation of the distinct forms of the invention, i.e. Form 1 and Form 4, but are not intended to limit the scope of the invention as defined herein or as claimed below.

Example 1—Preparation of Form 1

4-amino-3-hydroxybenzoicacid (1.0 eq, LR) was dissolved at 20° C. in a mixture of tetrahydrofuran (19 L/kg) and water (1.9 L/Kg). 3,5-dichlorobenzoylchloride (1.3 equiv) was added as a tetrahydrofuran solution (1.9 L/kg) and the mixture stirred for at least 30 minutes at 20° C. Once the reaction was deemed complete by HPLC (<5% remaining 4-amino-3-hydroxybenzoicacid), triethylamine (1.2 equiv) was added and the mixture was heated to 35° C. and stirred for at least 90 minutes. The solvent was partially displaced with ethanol by constant level distillation until 5-15% THF remained. The slurry was cooled to 20° C. and stirred for at least 60 minutes then the slurry was filtered. The solids were washed with ethanol (3×4 L/kg) then dried under vacuum at 65° C. for at least 16 hours to give pure 4-[(3,5-dichlorobenzoyl)amino]-3-hydroxybenzoic acid in 88-92% yield.

To a slurry of 4-[(3,5-dichlorobenzoyl)amino]-3-hydroxybenzoic acid (1.0 equiv) in tetrahydrofuran (10 L/kg) was added triethylamine (1.1 equiv), followed by water (4 equiv). The mixture was held at 20-25° C. for 1 hour, then the mixture was filtered to remove any remaining insoluble material. Methanesulfonic acid (1.6 equiv) was added and a slurry formed. A constant level displacement of THF/water with toluene was carried out until the reaction temperature was at least 107° C., at which point the displacement was stopped and the reaction then refluxed for at least 15 hours. Once the reaction was deemed complete by UPLC, i.e. >95% pure, it was cooled to 20° C. and 2-propanol (5 L/kg) was added. The slurry was granulated for at least 60 minutes, then filtered and washed twice with 2-propanol (4 L/kg each wash) and dried under vacuum at 60-70° C. for a minimum of 18 hours to give Form 1 in 82-89% yield.

Example 2—Preparation of Form 4

Form 1 (187 mg) was suspended in tetrahydrofuran (7.5 mL) and the suspension was heated at 75° C. The clear solution was hot-filtered through a pre-warmed 0.2 μm nylon filter into a container with toluene (25 mL) chilled on an ice/water bath. The sample was stored in freezer (−10 to −25° C.) overnight. Form 4 was collected, while cold, by vacuum filtration.

Example 3—Preparation of Form 2

A 3 mg/mL THF solution of Form 1 was allowed to evaporate at ambient conditions in a hood and crystals were obtained. Single crystal analysis showed the following results:

| | |
|---|---|
| Empirical formula | $C_{14}H_7NO_3Cl_2$ |
| Formula weight | 308.12 |
| Temperature | Ambient |
| Wavelength | 1.54178 Å |
| Crystal system | Triclinic |
| Space group | P-1 |
| Unit cell dimensions | a = 3.7740(2) Å    α = 80.668(3)° |
| | b = 13.6536(8) Å    β = 89.381 (4)° |
| | c = 15.5098(9) Å    γ = 89.520(3)° |
| Volume | 788.56(8) Å$^3$ |
| Z | 4 |
| Density (calculated) | 1.365 Mg/m$^3$ |
| Goodness-of-fit on F$^2$ | 1.112 |
| Final R indices [I > 2 sigma(I)] | R1 = 0.0776, wR2 = 0.2360 |
| R indices (all data) | R1 = 0.1026, wR2 = 0.2561 |

Example 4—Preparation of Form 6

Form 1 (4168 mg) was suspended in tetrahydrofuran (100 mL), heated and stirred at 60° C. Dimethylacetamide (5 mL) was added. Solution resulted was hot filtered through a pre-warmed 0.2 μm nylon filter into a container with dichloromethane chilled on an ice/water bath. Solids observed were isolated by vacuum filtration and air dried at ambient temperature.

Example 5—Preparation of Amorphous 6-Carboxy-2-(3,5-dichlorophenyl)-benzoxazole

Form 1 (79.7 mg) was suspended in 5 mL of dioxane/water 80/20 and heated at ~80° C. The resulting clear solution was hot filtered through a pre-warmed 0.2 μm nylon filter into a pre-warmed receiving vial. The sample was then frozen on a dry ice/IPA bath and transferred to the freeze dryer for 2 days. Solids were collected.

We claim:

1. A crystalline form of 6-carboxy-2-(3,5-dichlorophenyl)-benzoxazole, wherein said crystalline form has an analytical parameter selected from the group consisting of
   a solid state NMR spectrum comprising 13C chemical shifts (ppm) at 120.8±0.2 and 127.7±0.2,
   a powder X-ray diffraction pattern comprising a peak at a diffraction angle (2θ) of 28.6±0.2, and
   a Raman spectrum comprising a Raman shift peak (cm-1) at 1292±2.

2. The crystalline form of 6-carboxy-2-(3,5-dichlorophenyl)-benzoxazole of claim 1, wherein said solid state NMR spectrum further comprises 13C chemical shifts (ppm) at 139.6±0.2.

3. The crystalline form of 6-carboxy-2-(3,5-dichlorophenyl)-benzoxazole of claim 1, wherein said solid state NMR spectrum further comprises 13C chemical shifts (ppm) at 144.7±0.2.

4. The crystalline form of 6-carboxy-2-(3,5-dichlorophenyl)-benzoxazole of claim 1, wherein said powder X-ray diffraction pattern further comprises peaks at diffraction angles (2θ) of 16.5±0.2 and 26.7±0.2.

5. The crystalline form of 6-carboxy-2-(3,5-dichlorophenyl)-benzoxazole of claim 1, wherein said powder X-ray diffraction pattern further comprises peaks at diffraction angles (2θ) of 15.4±0.2 and 20.2±0.2.

6. The crystalline form of 6-carboxy-2-(3,5-dichlorophenyl)-benzoxazole of claim 5, wherein said powder X-ray diffraction pattern further comprises a peak at a diffraction angle (2θ) of 29.0±0.2.

7. The crystalline form of 6-carboxy-2-(3,5-dichlorophenyl)-benzoxazole of claim 6, wherein said powder X-ray diffraction pattern further comprises a peak at a diffraction angle (2θ) of 23.5±0.2.

8. The crystalline form of 6-carboxy-2-(3,5-dichlorophenyl)-benzoxazole of claim 1, wherein said crystalline form has a Raman spectrum further comprising Raman shift peaks (cm-1) at 994±2, 1273±2 and 1615±2.

9. The crystalline form of 6-carboxy-2-(3,5-dichlorophenyl)-benzoxazole of claim 8, wherein said Raman spectrum further comprises Raman shift peaks (cm-1) at 287±2 and 869±2.

10. The crystalline form of 6-carboxy-2-(3,5-dichlorophenyl)-benzoxazole of claim 9, wherein said Raman spectrum further comprises a Raman shift peak (cm-1) at 213±2.

11. A crystalline form of 6-carboxy-2-(3,5-dichlorophenyl)-benzoxazole, wherein said form (i) has a powder X-ray diffraction pattern comprising peaks at diffraction angles (2θ) of 26.7±0.2 and 28.6±0.2; and (ii) has a solid state NMR spectrum comprising a 13C chemical shift (ppm) at 127.7±0.2.

12. A crystalline form of 6-carboxy-2-(3,5-dichlorophenyl)-benzoxazole, wherein said form (i) has a Raman spectrum comprising Raman shift peaks (cm-1) at 1292±2 and 1615±2; and (ii) has a solid state NMR spectrum comprising a 13C chemical shift (ppm) at 127.7±0.2.

13. The crystalline form of claim 1, wherein said form is non-hygroscopic and anhydrous.

14. The crystalline form of claim 1, wherein said form is substantially pure.

15. A pharmaceutical composition comprising the crystalline form of claim 1 in a therapeutically effective amount in admixture with at least one pharmaceutically acceptable excipient.

16. A method of treating transthyretin amyloid disease in a mammal, the method comprising administering to the mammal a therapeutically effective amount of the crystalline form claim 1.

* * * * *